US012605372B2

(12) United States Patent
Amatangelo et al.

(10) Patent No.: US 12,605,372 B2
(45) Date of Patent: Apr. 21, 2026

(54) COMBINATION THERAPY FOR THE TREATMENT OF CANCER

(71) Applicant: Celgene Corporation, Summit, NJ (US)

(72) Inventors: Michael D. Amatangelo, Madison, NJ (US); Chad Bjorklund, Summit, NJ (US); Anjan Thakurta, Basking Ridge, NJ (US); Xiankang Hong, Bridgewater, NJ (US); Mariana Cota, Summit, NJ (US)

(73) Assignee: Celgene Corporation, Summit, NJ (US)

( * ) Notice: Subject to any disclaimer, the term of this patent is extended or adjusted under 35 U.S.C. 154(b) by 106 days.

(21) Appl. No.: 17/983,762

(22) Filed: Nov. 9, 2022

(65) Prior Publication Data

US 2023/0277517 A1 Sep. 7, 2023

Related U.S. Application Data

(62) Division of application No. 16/588,318, filed on Sep. 30, 2019, now Pat. No. 11,529,339.

(60) Provisional application No. 62/773,980, filed on Nov. 30, 2018, provisional application No. 62/739,809, filed on Oct. 1, 2018.

(51) Int. Cl.

| | |
|---|---|
| ***A61K 31/45*** | (2006.01) |
| ***A61K 9/00*** | (2006.01) |
| ***A61K 47/68*** | (2017.01) |
| ***A61P 31/00*** | (2006.01) |
| ***A61P 35/00*** | (2006.01) |

(52) U.S. Cl.
CPC .......... *A61K 31/45* (2013.01); *A61K 47/6849* (2017.08); *A61P 31/00* (2018.01); *A61P 35/00* (2018.01); *A61K 9/0019* (2013.01)

(58) Field of Classification Search
CPC ................ A61K 31/4035; A61K 31/45; A61K 47/6849; A61P 35/00
See application file for complete search history.

(56) References Cited

U.S. PATENT DOCUMENTS

| | | | |
|---|---|---|---|
| 8,518,972 B2 | 8/2013 | Man et al. | |
| 9,221,788 B2 | 12/2015 | Cohen et al. | |
| 9,309,219 B2 | 4/2016 | Man et al. | |
| 9,309,220 B2 | 4/2016 | Traverse et al. | |
| 9,629,849 B2 | 4/2017 | Cohen et al. | |
| 9,822,094 B2 | 11/2017 | Man et al. | |
| 9,828,361 B2 | 11/2017 | Man et al. | |
| 9,884,062 B2 | 2/2018 | Cohen et al. | |
| 9,975,872 B2 | 5/2018 | Traverse et al. | |
| 10,080,801 B2 | 9/2018 | Parikh et al. | |
| 10,189,814 B2 | 1/2019 | Man et al. | |
| 10,245,266 B2 | 4/2019 | Schafer et al. | |
| 10,463,672 B2 | 11/2019 | Cohen et al. | |
| 11,529,339 B2 | 12/2022 | Amatangelo et al. | |
| 2011/0196150 A1 | 8/2011 | Man et al. | |
| 2014/0045843 A1* | 2/2014 | Schafer .................. | A61K 45/06 514/235.2 |
| 2014/0045844 A1 | 2/2014 | Schafer et al. | |
| 2014/0343058 A1 | 11/2014 | Schafer et al. | |
| 2015/0038511 A1 | 2/2015 | Schafer et al. | |
| 2015/0099745 A1 | 4/2015 | Parikh et al. | |
| 2016/0051530 A1* | 2/2016 | Thakurta ............ | A61K 31/5377 514/323 |
| 2016/0256468 A1 | 9/2016 | Schafer et al. | |
| 2019/0135780 A1 | 5/2019 | Man et al. | |
| 2019/0262348 A1 | 8/2019 | Schafer et al. | |
| 2019/0365772 A1 | 12/2019 | Cohen et al. | |
| 2019/0388429 A1 | 12/2019 | Schafer et al. | |

FOREIGN PATENT DOCUMENTS

| | | | |
|---|---|---|---|
| CN | 104837491 A | 8/2015 | |
| CN | 107073115 A | 8/2017 | |
| WO | WO 2008/115516 A2 | 9/2008 | |
| WO | WO 2011/112933 A1 | 9/2011 | |
| WO | WO 2012/125459 A1 | 9/2012 | |
| WO | WO 2014/025960 A1 | 2/2014 | |
| WO | WO-2014089416 A1 * | 6/2014 | ................ A61P 7/00 |
| WO | WO 2016/029004 A1 | 2/2016 | |
| WO | WO 2018/083204 A1 | 5/2018 | |
| WO | WO 2020/072334 A1 | 4/2022 | |

OTHER PUBLICATIONS

Daratumumab product page (published May 2018) (Year: 2018).*
Dexamethasone (decadron) product page (published 2016). (Year: 2016).*
Amatangelo et al., "Iberdomide (CC-220) Has Synergistic Anti-Tumor and Immunostimulatory Activity Against Multiple Myeloma in Combination with Both Bortezomib and Dexamethasone, or in Combination with Daratumumab in Vitro I Blood I American Society of Hematology", Blood Supplement 1, Nov. 29, 2018 (Nov. 29, 2018), pp. 1-6, XP055678955, DOI: 10.1182/blood-2018-99-113383 Retrieved from the Internet: URL:https://ashpublications.org/blood/article/132/Supplement%201/1935/261933/Iberdomide-CC220-Has-Synergistic-AntiTumor-and [retrieved on Mar. 23, 2020] *abstract*.

(Continued)

*Primary Examiner* — George W Kosturko
(74) *Attorney, Agent, or Firm* — Jones Day

(57) ABSTRACT

Provided herein are methods of treating and/or managing cancers, which comprise administering to a patient Compound A, or an enantiomer or a mixture of enantiomers thereof, or a pharmaceutically acceptable salt, solvate, hydrate, co-crystal, clathrate, or polymorph thereof in combination with daratumumab. Additionally, provided herein are methods of treating and/or managing cancers, which comprise administering to a patient Compound A, or an enantiomer or a mixture of enantiomers thereof, or a pharmaceutically acceptable salt, solvate, hydrate, co-crystal, clathrate, or polymorph thereof in combination with daratumumab and dexamethasone.

19 Claims, 2 Drawing Sheets

(56) References Cited

OTHER PUBLICATIONS

Anonymous: "A Study to Determine Dose, Safety, Tolerability and Efficacy of CC-220 Monotherapy, and in Combination With Other Treatments in Subjects With Multiple Myeloma—Full Text View—Clinical Trials.gov", May 16, 2016 (May 16, 2016), XP055783546, Retrieved from the Internet: URL:https://clinicaltrials.gov/ct2/show/NCT02773030?term-02773030&draw=1&rank=1[retrieved on Mar. 9, 2021].

Brown et al., "A clinical study assessing the tolerability and biological effects of infliximab, a TNF-$\alpha$ inhibitor, in patients with advanced cancer," Annals of Oncology, 19(7):1340-1346 (2008).

Calado et al., "Constitutive canonical NF-κB activation cooperates with disruption of BLIMP1 in the pathogenesis of activated B-cell like diffuse large B-cell lymphoma," Cancer Cell, 18(6):580-589 (2010).

Choi et al., "A new mimmunostain algorithm classifies diffuse large b-cell lymphoma into molecular subtypes with high accuracy," Clinical Cancer Research, 15(17):5494-5502 (2009).

Dimopoulos M. A. et al. Daratumumab, Lenalidomide, and Dexamethasone for Multiple Myeloma. 2016, vol. 375(14), p. 1319-1331. doi: 10.1056/NEJMoa1607751.

Daratumumab (Darzalex) prescribing information. Published May 2018.

Dexamethasone (Decadron) prescribing information. Published 2016.

Harrison et al., "Tumor Necrosis Factor a As a New Target for Renal Cell Carcinoma: Two Sequential Phase II Trials of Infliximab at Standard and High Dose," Journal of Clinical Oncology, 25(29):4542-4549 (2007).

Kloo et al., "Critical role of PI3K signaling for NF-κB-dependent survival in a subset of activated B-cell-like diffuse large B-cell lymphoma cells," PNAS, 108(1):272-277 (2011).

Lonial et al., "First clinical (phase 1b/2a) study of iberdomide (CC-220; IBER), a CELMoD, in combination with dexamethasone (DEX) in patients (pts) with relapsed/refractory multiple myeloma (RRMM)", Journal of Clinical Oncology 2019, 37, No. 15 suppl, 8006.

Lopez-Girona et al., "Cereblon is a direct protein target for immunomodulatory and antiproliferative activities of lenalidomide and pomalidomide," Leukemia, 26:2326-2335 (2012).

Madhusudan et al., "Study of Etanercept, a Tumor Necrosis Factor-Alpha Inhibitor, in Recurrent Ovarian Cancer," Journal of Clinical Oncology, 23(25):5950-5959 (2005).

Morin et al., "Tyrosine 641 of the EZH2 oncogene is frequently mutated in follicular and diffuse large B-cell lymphomas of germinal center origina," 2009 ASH Annual Meeting Abstracts, 114(22):64-65 (2009).

Mak et al., "Lost in translation: animal models and clinical trials in cancer treatment," Am J Transl Res. 2014; 6(2): 114-118.

Naugler et al., "NK-kB and cancer—identifying targets and mechanisms," Current Opinon in Generics & Developments 2008; 18:19-26.

Sanchez et al., 2016, "Daratumumab: a first-in-class CD38 monoclonal antibody for the treatment of multiple myeloma," Journal of Hematology & Oncology, 9(51), 8 pages.

Amatangelo, et al., 2024, "Iberdomide, Daratumumab, and Dexamethasone Shows Deep Antimyeloma Activity across Molecular Patient Subsets with Transplant-Ineligible Newly Diagnosed Multiple Myeloma from the CC-220-MM-001 Trial", Blood 144(S1):1973-1974 (2 pages).

Amatangelo, et al., 2024, "Iberdomide is Immune Stimulatory and Induces Deep Anti-Myeloma Activity Across Doses in Combination With Daratumumab in Patients With TNE NDMM From the CC-220-MM-001 Study", HemaSphere, 8:(S1):1489-1490 (2 pages).

Balari et al., 2024, "OA-55: Iberdomide, Daratumumab, and Dexamethasone (IberDd) in Transplant-Ineligible (TNE) Newly Diagnosed Multiple Myeloma (NDMM): Results From the CC-220-MM-001 Trial," Clinical Lymphoma, Myeloma & Leukemia, 24(suppl. 2):S34 (1 page).

Chou, Ting-Chao, 2006, "Theoretical basis, experimental design, and computerized simulation of synergism and antagonism in drug combination studies," Pharmacol Rev. 58(3):621-81 (62 pages).

Costa et al., 2024, "P-326: Phase 1b/2 Trial of Iberdomide in Combination With Daratumumab, Dexamethasone +/− Carfilzomib To Eliminate MRD After Induction Therapy and ASCT in NDMM," Clinical Lymphoma, Myeloma & Leukemia, 24(suppl. 2):S222-223 (2 pages).

* cited by examiner

COMBINATION THERAPY FOR THE TREATMENT OF CANCER

This application is a divisional application of U.S. patent application Ser. No. 16/588,318, filed on Sep. 30, 2019, which claims the benefit of U.S. Provisional Application Ser. No. 62/739,809, filed on Oct. 1, 2018 and U.S. Provisional Application Ser. No. 62/773,980, filed on Nov. 30, 2018, each of which is incorporated herein by reference in its entirety.

FIELD

Provided herein are combination therapies for treating and/or managing cancers, which comprise administering to a patient 3-(4-((4-(morpholinomethyl)benzyl)oxy)-1-oxoisoindolin-2-yl)piperidine-2,6-dione ("Compound A"), or an enantiomer or a mixture of enantiomers thereof, or a pharmaceutically acceptable salt, solvate, hydrate, co-crystal, clathrate, or polymorph thereof, in combination with daratumumab. Also provided are combination therapies for treating and/or managing cancers, which comprise administering to a patient 3-(4-((4-(morpholinomethyl)benzyl)oxy)-1-oxoisoindolin-2-yl)piperidine-2,6-dione ("Compound A"), or an enantiomer or a mixture of enantiomers thereof, or a pharmaceutically acceptable salt, solvate, hydrate, co-crystal, clathrate, or polymorph thereof, in combination with daratumumab and dexamethasone. Further provided herein is 3-(4-((4-(morpholinomethyl)benzyl)oxy)-1-oxoisoindolin-2-yl)piperidine-2,6-dione ("Compound A"), or an enantiomer or a mixture of enantiomers thereof, or a pharmaceutically acceptable salt, solvate, hydrate, co-crystal, clathrate, or polymorph thereof for use in said combination therapies.

BACKGROUND

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology,* 17.1-17.12 (3rd ed., Mosby, St. Louis, Mo., 1993).

There is an enormous variety of cancers which are described in detail in the medical literature. Examples include cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Hematologic Cancers begin in blood-forming tissue, such as the bone marrow, or in the cells of the immune system. Examples of hematologic cancer are leukemia, lymphoma and multiple myeloma. Hematologic cancer is also called blood cancer.

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023. NHL is a cancer that starts in white blood cells. It is defined as being not Hodgkin lymphoma. NHL may be of B-cell, NK-cell or T-cell lymphoma. There are more than 60 subtypes of NHL, the most common are Diffuse Large B-cell Lymphoma (DLBCL), Follicular Lymphoma (FL), Mantle Cell Lymphoma (MCL), Small lymphocytic lymphoma, Double hit lymphoma, Primary mediastinal large B-cell Lymphoma, Splenic marginal zone B-cell lymphoma, Extranodal Marginal Zone B-cell lymphoma (MALT), Nodal Marginal Zone B-cell lymphoma and Lymphoplasmacytic lymphoma, Burkitt lymphoma, Primary Effusion Lymphoma are the most common B-cell lymphomas.

The most common T-cell lymphomas include Anaplastic large cell Lymphoma (systemic and cutaneous type), Peripheral T-Cell Lymphoma, Angioimmunoblastic T-cell lymphoma, Adult T-cell lymphoma/leukemia and Extranodal NK/T-cell lymphoma Diffuse large B-cell lymphoma (DLBCL) accounts for approximately one-third of non-Hodgkin's lymphomas.

While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. See D. Kim et al., *Journal of Clinical Oncology*, 2007 ASCO Annual Meeting Proceedings Part I. Vol 25, No. 18S (June 20 Supplement), 2007: 8082.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 ($17^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 ($17^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CIVIL). *The Merck Manual*, 949-952 ($17^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

Accordingly, compounds that can control and/or inhibit unwanted angiogenesis or inhibit the production of certain cytokines, including TNF-α, may be useful in combination therapy for the treatment and prevention of various forms of cancer.

Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

There exists a significant need for safe and effective methods of treating, preventing and managing cancer, particularly for cancers that are refractory to standard treatments, such as surgery, radiation therapy, chemotherapy and hormonal therapy, while reducing or avoiding the toxicities and/or side effects associated with the conventional therapies.

Multiple Myeloma

Multiple myeloma (MM) remains an incurable neoplastic disease that accounts for 12% of all hematological malignancies. It has been estimated that 138,509 new cases and 98,437 deaths from MM occurred globally in 2016 (Cowan et al., *JAMA Oncol* 2018, 4(9), 1221-1227).

Human plasma cells (PCs) and their precursors play an essential role in humoral immune response, but likewise give rise to a variety of malignant B-cell disorders, including multiple myeloma. Differentiation of B cells into antibody-secreting plasma cells is a crucial component of the immune response. See Jacob et al., *Autoimmunity* 2010, 43(1), 84-97. A small number of transcription factors have been identified that guide the developmental program leading to plasma cell differentiation. PAX5 and BCL6 are expressed in activated B cells and act predominantly by repressing differentiation. PAX5 represses genes associated with a number of genes, including PRDM1 (the gene encoding BLIMP-1 protein), XBP1, and IgJ (J chain). BCL6 suppress plasma cell development in part by repressing PRDM1. See Jourdan et al., *Blood* 2009, 114 (10), 5173-5181; Kallies et al., *Immunity* 2007, 26(5), 555-566; Lenz et al., *N. Engl. J. Med.* 2010, 362, 1417-1429. The differentiation and high immunoglobulin (Ig) secretion also requires IRF-4, XBP-1, and BLIMP-1. IRF-4 expression markedly increases upon differentiation, which is essential for plasma cell formation and Ig secretion. XBP-1 directly controls aspects of the secretory pathway and is strongly induced in plasma cell by a combination of loss of PAX5-mediated gene repression and posttranscriptional control. BLIMP-1 is expressed in plasma cells but is absent from earlier stages of B cell ontogeny. See Jourdan et al., *Blood* 2009, 114 (10), 5173-5181; Kallies et al., *Immunity* 2007, 26(5), 555-566; Lenz et al., *N. Engl. J. Med.* 2010, 362, 1417-1429. Lenalidomide, an immunomodulatory compound, has been demonstrated to be effective in the treatment of multiple myeloma and ABC lymphomas. The potential activities of immunomodulatory compounds on normal B cells include activation or inhibition of naïve CD19+ B cells (depending on stimulus). In B tumor cells, immunomodulaory compounds inhibit multiple myeloma and lymphoma proliferation, tumor suppressor gene induction (cyclin dependent kinase inhibitors p21, p27 etc.), F-actin polymerization and CD20 clustering in MCL and CLL, also inhibit C/EBPβ, IRF4, BLIMP-1, and XBP-1 expression in MM, and inhibit NF-κB activation in ABC lymphoma cells.

Significant progress has been made in the treatment of MM with various combinations of melphalan, prednisone, dexamethasone (DEX), doxorubicin, cyclophosphamide, etoposide, cisplatin, immunomodulatory agents, monoclonal antibodies and proteasome inhibitors or with autologous stem cell transplant following high-dose chemotherapy (National Comprehensive Cancer Network [NCCN] Guidelines, 2015, available at the NCCN website http://www.nccn.org/professionals/physician_gls/PDF/myeloma.pdf Accessed 29 Jan. 2016).

The main considerations for choosing an appropriate treatment for relapsed and refractory multiple myeloma (RRMM) are risk level prior therapy, duration of response to prior therapy, residual toxicity, age, physical condition, and whether the patient is a candidate for stem cell transplantation (NCCN Guidelines, 2015).

Several compounds have recently been approved for the treatment of RRMM, carfilzomib, a proteasome inhibitor used with dexamethasone or with lenalidomide plus dexamethasone; panabinostat, a histone deacetylase inhibitor used in combination with bortezomib and dexamethasone; daratumumab, a human CD38-directed monoclonal antibody; elotuzumab, a SLAMF7 protein immunostimulatory antibody used with lenalidomide and dexamethasone and; ixazomib, a proteasome inhibitor used with lenalidomide and dexamethasone.

Despite this progress in treatment options for MM, the disease follows a relapsing course in the majority of patients, regardless of treatment regimen or initial response to treatment (Kumar et al., *Leukemia* 2012, 26(1), 149-57). Multiple myeloma remains incurable using conventional treatments, with an overall 5-year relative survival rate of 45% (Howlader et al., available at the SEER website http://seer.cancer.gov/csr/1975_2012/, based on November 2014 SEER data submission, posted to the SEER website, April 2015). Therefore, despite the recent new treatment approvals, additional therapies are needed to treat RRMM patients.

SUMMARY

Provided herein are methods of treating and managing cancer, including newly diagnosed cancer, as well as cancer that is relapsed, refractory or resistant to conventional chemotherapy, which comprise administering to a patient in need of such treatment or management (i) a therapeutically or prophylactically effective amount of 3-(4-((4-(morpholinomethyl)benzyl)oxy)-1-oxoisoindolin-2-yl)piperidine-2,6-dione, having the following structure:

Compound A

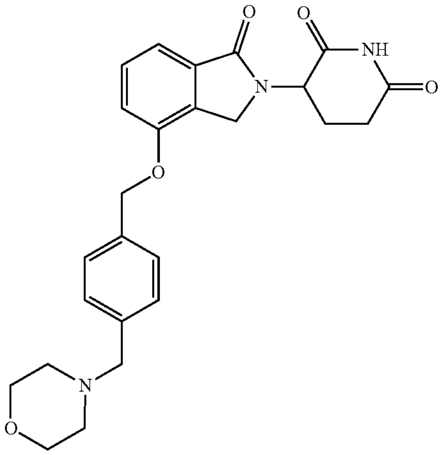

or an enantiomer or a mixture of enantiomers thereof, or a pharmaceutically acceptable salt, solvate, hydrate, co-crystal, clathrate, or polymorph thereof and (ii) daratumumab. Provided herein is 3-(4-((4-(morpholinomethyl)benzyl)oxy)-1-oxoisoindolin-2-yl)piperidine-2,6-dione ("Compound A") or an enantiomer or a mixture of enantiomers thereof, or a pharmaceutically acceptable salt, solvate, hydrate, co-crystal, clathrate, or polymorph thereof for use in such methods of treating and managing cancer, including newly diagnosed cancer, as well as cancer that is relapsed, refractory or resistant to conventional chemotherapy.

In one embodiment, a method of treating and managing cancer, including newly diagnosed cancer, as well as cancer that is relapsed, refractory or resistant to conventional chemotherapy, comprises administering to a patient in need of such treatment or management (i) a therapeutically or prophylactically effective amount of 3-(4-((4-(morpholinomethyl)benzyl)oxy)-1-oxoisoindolin-2-yl)piperidine-2,6-dione, having the following structure:

Compound A

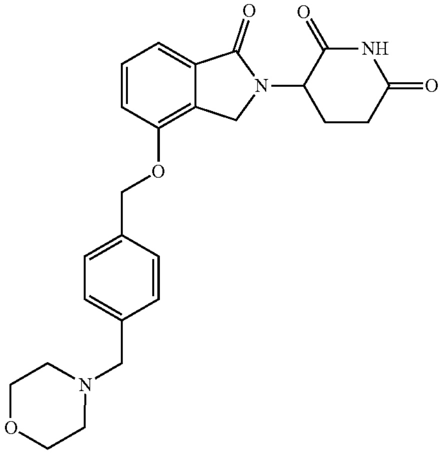

or an enantiomer or a mixture of enantiomers thereof, or a pharmaceutically acceptable salt, solvate, hydrate, co-crystal, clathrate, or polymorph thereof; (ii) daratumumab, and (iii) dexamethasone, or an enantiomer or a mixture of enantiomers thereof, or a pharmaceutically acceptable salt, solvate, hydrate, co-crystal, clathrate, or polymorph thereof. Provided herein is 3-(4-((4-(morpholinomethyl)benzyl)oxy)-1-oxoisoindolin-2-yl)piperidine-2,6-dione ("Compound A") or an enantiomer or a mixture of enantiomers thereof, or a pharmaceutically acceptable salt, solvate, hydrate, co-crystal, clathrate, or polymorph thereof for use in such a method of treating and managing cancer, including newly diagnosed cancer, as well as cancer that is relapsed, refractory or resistant to conventional chemotherapy.

In one embodiment, the Compound A is the enantiomer (S)-3-(4-((4-(morpholinomethyl)benzyl)oxy)-1-oxoisoindolin-2-yl)piperidine-2,6-dione, having the structure:

Compound A-S

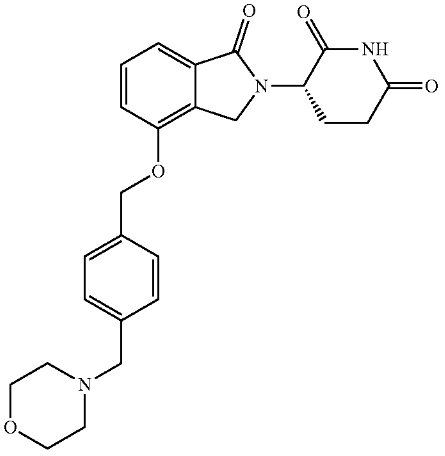

In another embodiment, the compound A is the enantiomer (R)-3-(4-((4-(morpholinomethyl)benzyl)oxy)-1-oxoisoindolin-2-yl)piperidine-2,6-dione, having the structure:

Compound A-R

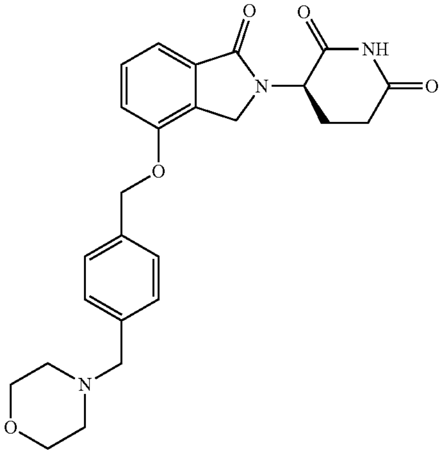

Also provided herein are methods of managing cancer (e.g., preventing its recurrence, or lengthening the time of remission), which comprise administering to a patient in need of such management a therapeutically or prophylactically effective amount of (i) 3-(4-((4-(morpholinomethyl) benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof and (ii) daratumumab. Provided herein is (i) 3-(4-((4-(morpholinomethyl)benzyl) oxy)-1-oxoisoindolin-2-yl)piperidine-2,6-dione or an enantiomer or a mixture of enantiomers thereof, or a pharmaceutically acceptable salt, solvate, hydrate, co-crystal, clathrate, or polymorph thereof for use in such methods of managing cancer (e.g., preventing its recurrence, or lengthening the time of remission).

Further provided herein are methods of managing cancer (e.g., preventing its recurrence, or lengthening the time of remission), which comprise administering to a patient in need of such management a therapeutically or prophylactically effective amount of (i) 3-(4-((4-(morpholinomethyl) benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof; (ii) daratumumab and (iii) dexamethasone, or an enantiomer or a mixture of enantiomers thereof, or a pharmaceutically acceptable salt, solvate, hydrate, co-crystal, clathrate, or polymorph thereof. Provided herein is 3-(4-((4-(morpholinomethyl)benzyl) oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof for use in such methods of managing cancer (e.g., preventing its recurrence, or lengthening the time of remission).

In certain embodiments, provided herein are methods for the treatment or management of cancer. In one embodiment, the cancer is a haematological cancer (e.g., multiple myeloma, lymphoma or leukemia).

In one embodiment, provided herein are methods for the treatment or management of multiple myeloma. In one embodiment, the multiple myeloma is smouldering multiple myeloma. In one embodiment, the multiple myeloma is active multiple myeloma. In one embodiment, the multiple myeloma is extramedullary plasmacytoma. In one embodiment, the multiple myeloma is solitary plasmacytoma of the bone. In one embodiment, the multiple myeloma is light chain myeloma. In one embodiment, the multiple myeloma is non-secretory myeloma.

In one embodiment, the multiple myeloma is relapsed and/or refractory. In one embodiment, the multiple myeloma is relapsed. In one embodiment, the multiple myeloma is refractory. In one embodiment, the multiple myeloma is resistant to conventional chemotherapy.

In one embodiment, provided herein are methods for the treatment or management of lymphoma. In certain embodiments, provided herein are methods for the treatment or management of Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

The methods provided herein encompass methods for screening or identifying cancer patients, e.g., lymphoma, non-Hodgkin's lymphoma, multiple myeloma, leukemia, and AML patients, for treatment with 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab. In particular, provided herein are methods for selecting patients having a higher response rate to therapy with 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab.

The methods provided herein encompass methods for screening or identifying cancer patients, e.g., lymphoma, non-Hodgkin's lymphoma, multiple myeloma, leukemia and AML patients, for treatment with 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab. In particular, provided herein are methods for selecting patients having a higher response rate to therapy with 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination daratumumab and dexamethasone.

In one embodiment, provided herein is a method for treating or managing multiple myeloma, comprising:

(i) identifying a patient having multiple myeloma sensitive to treatment with 3-(4-((4-(morpholinomethyl) benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab; and (ii) administering to the patient a therapeutically effective amount of 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab.

Provided herein is 3-(4-((4-(morpholinomethyl)benzyl) oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof for use in such a method for treating or managing multiple myeloma.

In one embodiment, provided herein is a method for treating or managing multiple myeloma, comprising:

(i) identifying a patient having multiple myeloma sensitive to treatment with 3-(4-((4-(morpholinomethyl) benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab and dexamethasone, or an enantiomer or a mixture of enantiomers thereof, or a pharmaceutically acceptable salt, solvate, hydrate, co-crystal, clathrate, or polymorph thereof; and (ii) administering to the patient a therapeutically effective amount of 3-(4-((4-(morpholinomethyl)benzyl)oxy)-1- oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof in combination with daratumumab and dexamethasone, or an enantiomer or a mixture of enantiomers thereof, or a pharmaceutically acceptable salt, solvate, hydrate, co-crystal, clathrate, or polymorph thereof.

Provided herein is 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof for use in such a method for treating or managing multiple myeloma.

Provided herein are pharmaceutical compositions comprising about 0.5 to 100 mg of 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof and one or more additional active agents. In certain embodiments, the one or more additional active agents are selected from oblimersen, melphalan, G-CSF, GM-CSF, GC-CSF, BCG, EPO, interleukins, monoclonal antibodies, cancer antibodies, a cox-2 inhibitor, topotecan, pentoxifylline, ciprofloxacin, daratumumab, taxotere, iritotecan, dexamethasone, doxorubicin, vincristine, IL 2, IFN, dacarbazine, Ara-C, vinorelbine, isotretinoin, a proteasome inhibitor, a HDAC inhibitor, taxanes, rituxan, and prednisone.

Also provided herein are pharmaceutical compositions comprising (i) about 0.5 to 100 mg of 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof, and (ii) about 16 mg/kg to 200 mg/kg of daratumumab.

Further provided herein, are pharmaceutical compositions comprising (i) about 0.5 to 100 mg of 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof, (ii) about 16 mg/kg to 200 mg/kg of daratumumab, and (iii) about 20 to 200 mg of dexamethasone, or an enantiomer or a mixture of enantiomers thereof, or a pharmaceutically acceptable salt, solvate, hydrate, co-crystal, clathrate, or polymorph thereof.

Also provided herein is a kit comprising a pharmaceutical composition comprising (i) 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof; and (ii) daratumumab.

In one embodiment, provided herein is a kit comprising a pharmaceutical composition comprising (i) 3-(4-((4-(morpholinomethyl)benzyl)oxy)-1-oxoisoindolin-2-yl)piperidine-2,6-dione, or an enantiomer or a mixture of enantiomers thereof, or a pharmaceutically acceptable salt, solvate, hydrate, co-crystal, clathrate, or polymorph thereof; (ii) daratumumab, and (iii) dexamethasone, or an enantiomer or a mixture of enantiomers thereof, or a pharmaceutically acceptable salt, solvate, hydrate, co-crystal, clathrate, or polymorph thereof.

DETAILED DESCRIPTION

Definitions

Figure 1A:
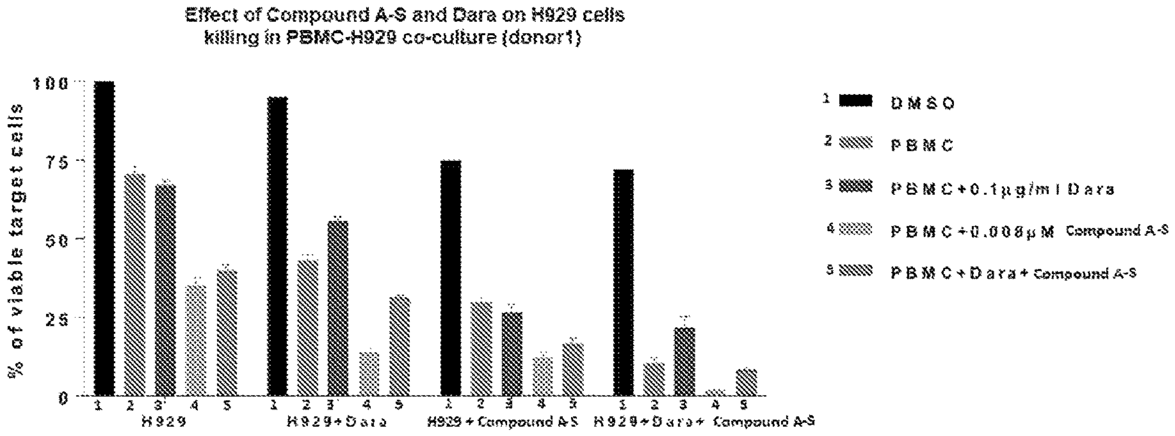
FIG. 1A depicts effects of compound A-S, daratumumab and the combination of compound A-S with daratumumab on MM cell line H929.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the term "subject" or "patient" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of the compounds provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of the compounds provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease, or lengthening the time during which the disease remains in remission.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

Combination therapy or "in combination with" refer to the use of more than one therapeutic agent to treat a particular disorder or condition. By "in combination with," it is not intended to imply that the therapeutic agents must be administered at the same time and/or formulated for delivery together, although these methods of delivery are within the scope of this disclosure. A therapeutic agent can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. The therapeutic agents in a combination therapy can also be administered on an alternating dosing schedule, with or without a resting period (e.g., no therapeutic agent is administered on certain days of the schedule). The administration of a therapeutic agent "in combination with" another therapeutic agent includes, but is not limited to, sequential administration and concomitant administration of the two agents. In general, each therapeutic agent is administered at a dose and/or on a time schedule determined for that particular agent.

As used herein, the terms "additional active agent," "active agent" and "active ingredient" refer to pharmacologically active compounds useful in the treatment of particular types of cancer, and certain diseases and conditions associated with or characterized by undesired angiogenesis. The active agents can be large molecules (e.g., proteins) or small molecules (e.g., synthetic inorganic, organometallic, or organic molecules). Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; GC-CSF, BCG, cancer antibodies, and EPO. Active agents that are small molecules can also be used to alleviate adverse effects associated with the administration of the compounds provided herein. However, like some large molecules, many are believed to be capable of providing a synergistic effect when administered with (e.g., before, after or simultaneously) the compounds provided herein. Examples of small molecule additional active agents include, but are not limited to, anti-cancer agents, antibiotics, immunosuppressive agents, and steroids.

In certain embodiments, the active agent is at least one chemotherapeutic agent, at least one anti-inflammatory agent, or at least one immunosuppressive and/or immunomodulatory agent. In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents. In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents. In one embodiment, such a chemotherapeutic agent may be selected from an antibiotic, such as dactinomycin (formerly actinomycin), bleomycin, daunorubicin (formerly daunomycin), idarubicin, mithramycin, mitomycin, mitoxantrone, plicamycin, anthramycin (AMC) and similar agents. In one embodiment, such a chemotherapeutic agent may be selected from an anti-mitotic agent, such as taxanes, for instance docetaxel, and paclitaxel. In one embodiment, such a chemotherapeutic agent may be selected from a topoisomerase inhibitor, such as topotecan. In one embodiment, such a chemotherapeutic agent may be selected from a growth factor inhibitor, such as an inhibitor of ErbB1 (EGFR) (such as gefitinib (Iressa®), cetuximab (Erbitux®), erlotinib (Tarceva®), 2F8 (disclosed in WO 2002/100348) and similar agents), an inhibitor of ErbB2 (Her2/neu) (such as trastuzumab (Herceptin®) and similar agents) and similar agents. In one embodiment, such a growth factor inhibitor may be a farnesyl transferase inhibitor, such as SCH-66336 and R115777. In one, embodiment, such a growth factor inhibitor may be a vascular endothelial growth factor (VEGF) inhibitor, such as bevacizumab (Avastin®). In one embodiment, such a chemotherapeutic agent may be a tyrosine kinase inhibitor, such as imatinib (Glivec, Gleevec STI571), lapatinib, PTK787/ZK222584 and similar agents. In one embodiment, such a chemotherapeutic agent may be a histone deacetylase inhibitor. Examples of such histone deacetylase inhibitors include hydroxamic acid-based hybrid polar compounds, such as SAHA (suberoylanilide hydroxamic acid). In one embodiment, such a chemotherapeutic agent may be a P38a MAP kinase inhibitor, such as SC10-469.

In a further embodiment, the combination therapy of the invention further includes administration of at least one inhibitor of angiogenesis, neovascularization, and/or other vascularization to a subject in need thereof. Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), Sugen 5416, SU5402, antiangiogenic ribozyme (such as angiozyme), interferon $\alpha$ (such as interferon $\alpha$2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents. Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In a further embodiment, the combination therapy of the invention further includes administration of an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J Immunol. 137(5), 1743-9 (1986), Pohl et al., Int J Cancer. 50(6), 958-67 (1992), Bohlen et al., Cytokines Mol Ther. 2(4), 231-8 (1996) and Maruyama, J Immunol Methods. 264(1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J Immunol. 17(11), 1645-8 (1987)), or a cell (for instance a red blood cell—see for instance Wi et al., J Immunol Methods. 122(2), 227-34 (1989)). In a further embodiment, the combination therapy of the invention further includes administration of a bisphosphonate. Examples of potentially suitable biphosphonates are pamidronate (Aredia®), zoledronic acid (Zometa®), clodronate (Bonefos®), risendronate (Actonel®), ibandronate (Boniva®), etidronate (Didronel®), alendronate (Fosamax®), tiludronate (Skelid®), incadronate (Yamanouchi Pharmaceutical) and minodronate (YM529, Yamanouchi). In a further embodiment, the combination therapy of the invention further includes administration of a colony stimulating factor. Examples of suitable colony stimulating factors are granulocyte-colony stimulating factors (G-CSF), such as filgrastim (Neupogen®) and pegfilgrastim (Neulasta®), and granulocyte macrophage-colony stimulating factors (GM-CSF) such as sargramostim (Leukine®). In a further embodiment, the combination therapy of the invention further includes administration of an erythropoietic agent. Examples of suitable erythropoietic agents are erythropoietin (EPO), such as epoetin alfa (for instance Procrit®, Epogen®, and Eprex®) and epoetin beta (for instance NeoRecormon®) and erythropoiesis-stimulating proteins (for instance Aranesp®). In a further embodiment, the combination therapy of the invention further includes administration of an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins. In a further embodiment, the combination therapy of the invention further includes administration of an agent that modulates, e.g., enhances or inhibits, the expression or activity of Fcα or Fcγ receptors. Examples of agents suitable for this use include interleukin-1 (IL-1), interleukin-2 (IL-2), interleukin-6 (IL-6), granulocyte colony-stimulating factor (G-CSF), such as filgrastim (Neupogen®) and pegfilgrastim (Neulasta®), and granulocyte macrophage-colony stimulating factors (GM-CSF) such as sargramostim (Leukine®), interferon-γ (IFN-γ), and tumor necrosis factor (TNF). In a further embodiment, the combination therapy of the invention further includes administration of a cell cycle control/apoptosis regulator (or "regulating agent"). A cell cycle control/apoptosis regulator may include molecules (i) that target and modulate cell cycle control/apoptosis regulators such as cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptdsis-inducing ligand (TRAIL)/apoptosis-2 ligand (Apo-2L), agents inducing NF-κB blockade leading to inhibition of IL-6 production, antibodies that activate TRAIL receptors, IFNs, anti-sense Bcl-2, and As2O3 (arsenic trioxide, Trisenox®). In a further embodiment, the combination therapy of the invention further includes administration of a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents. In a further embodiment, the combination therapy of the invention further includes administration of an anti-anergic agent (for instance small molecule compounds, proteins, glycoproteins, or antibodies that break tolerance to tumor and cancer antigens). Examples of such compounds are molecules that block the activity of CTLA-4, such as MDX-010 (Phan et al., PNAS USA 100, 8372 (2003)). In a further embodiment, the combination therapy of the invention further includes administration of a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In a further embodiment, the combination therapy of the invention further includes administration of an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf antisense oligonucleotide/ISIS-5132), MG98, and other antisense nucleic acids that target PKCα, clusterin, IGFBPs, protein kinase A, cyclin D1, or Bcl-2h. In a further embodiment, the combination therapy of the invention further includes administration of an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J Oncol. 4(1), 97-105 (2004), Collis et al., Int J Radiat Oncol Biol Phys. 57(2 Suppl), 5144 (2003), Yang et al., Oncogene. 22(36), 5694-701 (2003) and Zhang et al., Biochem Biophys Res Commun. 303(4), 1169-78 (2003)). In a further embodiment, the combination therapy of the invention further includes administration of a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions (see for instance Shah et al., J Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J Oncol. 24(4), 919-23 (2004) and Zwiebel et al., Semin Oncol. 28(4), 336-43 (2001). In a further embodiment, the combination therapy of the invention may further involve "whole cell" and "adoptive" immunotherapy methods. For instance, such methods may comprise infusion or re-infusion of immune system cells (for instance tumor-infiltrating lymphocytes (TILs), such as CD4+ and/or CD8+ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions. In a further embodiment, the combination therapy of the invention further includes the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In a further embodiment, the combination therapy of the invention further includes administration of complement. Accordingly, the use of compositions comprising anti-CD38 antibodies with serum or complement is also within the scope of the present invention. In these compositions the complement is located in close proximity to the anti-CD38 antibody, for instance by conjugation or may be suited for simultaneous administration. Alternatively, the anti-CD38 antibodies and the complement or serum may be administered separately. In a further embodiment, the combination therapy of the invention further includes administration of differentiation inducing agents, retinoic acid and retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents. In a further embodiment, the combination therapy of the invention further includes administration of a cathepsin B, modulators of cathepsin D dehydrogenase activity, glutathione-S-transferase (such as glutacylcysteine synthetase and lactate dehydrogenase), or similar agents. In a further embodiment, the combination therapy of the invention further includes administration of estramustine or epirubicin. In a further embodiment, the combination therapy of the invention further includes administration of a HSP90 inhibitor like 17-allyl amino geld-anamycin, antibodies directed against a tumor antigen such as PSA, CA125, KSA, etc., integrins like integrin β1, inhibitors of VCAM or similar agents In a further embodiment, the combination therapy of the invention further includes administration of calcineurin-inhibitors (such as valspodar, PSC 833 and other MDR-1 or p-glycoprotein inhibitors), TOR-inhibitors (such as sirolimus, everolimus and rapamycin). and inhibitors of "lymphocyte homing" mechanisms (such as FTY720), and agents with effects on cell signaling such as adhesion molecule inhibitors (for instance anti-LFA, etc.). In a further embodiment, the combination therapy of the invention further includes radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT), brachytherapy (BT) or skeletal targeted radiotherapy). Radioactive elements that may be used in practicing such methods include, e.g., radium, cesium-137, iridium-192, americium-241, gold-198, cobalt-57, copper-67, technetium-99, iodide-123, iodide-131, and indium-111. In a further embodiment, the combination therapy of the invention further includes autologous peripheral stem cell or bone marrow transplantation. In a further embodiment, the combination therapy of the invention further includes orthopedic intervention. Orthopedic interventions may be used in the treatment of a disorder involving cells expressing CD38, such as multiple myeloma, to help control pain or retain function or mobility. Such interventions may include physical therapy, splinting of bones to prevent or treat fractures, or surgical procedures (minor or major) to repair fractures. In a further embodiment, the combination therapy of the invention further includes delivery of one or more agents that promote access of the CD38 antibody or combination composition to the interior of a tumor. Such methods may for example be performed in association with the delivery of a relaxin, which is capable of relaxing a tumor (see for instance U.S. Pat. No. 6,719,977). In one embodiment, the anti-CD38 antibody used in the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129(12), 669-75 (2003), Pooga et al., FASEB J. 12(1), 67-77 (1998) and Tseng et al., Mol Pharmacol. 62(4), 864-72 (2002).

In a further embodiment, the combination therapy of the invention further includes administration of at least one anti-inflammatory agent. In one embodiment such an anti-inflammatory agent may be selected from a steroidal drug and a NSAID (nonsteroidal anti-inflammatory drug). In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies (e.g. 10F8 described in WO2004/058797), anti-IL15 antibodies, anti-IL15R antibodies, anti-CD4 antibodies, anti-CD11a antibodies (e.g., efalizumab), anti-alpha-4/beta-1 integrin (VLA4) antibodies (e.g natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In a further embodiment, the combination therapy of the invention further includes administration of at least one immunosuppressive and/or immunomodulatory agent to a subject in need thereof. In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents. In one embodiment, such an immunosuppressive and/or immunomodulatory agent may be selected from immunosuppressive antibodies, such as antibodies binding to p75 of the IL-2 receptor, or antibodies binding to for instance MHC, CD2, CD3, CD4, CD7, CD28, B7, CD40, CD45, IFNγ, TNF-α, IL-4, IL-5, IL-6R, IL-6; IGF, IGFR1, IL-7, IL-8, IL-10, CD11a, or CD58, or antibodies binding to their ligands. In one embodiment, such an immunosuppressive and/or immunomodulatory agent may be selected from soluble IL-15R, IL-10, B7 molecules (B7-1, B7-2, variants thereof, and fragments thereof), ICOS, and OX40, an inhibitor of a negative T cell regulator (such as an antibody against CTLA4) and similar agents. In a further embodiment, the combination therapy of the invention further includes administration of an anti-C3b(i) antibody.

In a further embodiment, the combination therapy of the invention further includes administration of histone deacetylase inhibitors (for instance phenylbutyrate) and/or DNA repair agents (for instance DNA repair enzymes and related compositions such as dimericine). In a further embodiment, the combination therapy of the invention further includes anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004).

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, PA, 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation*, Gibson Ed., CRC Press LLC: Boca Raton, FL, 2004).

As used herein, and unless otherwise specified, the term "tumor" refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the term "relapsed" refers to a situation where a subject or a mammal, which has had a remission of cancer after therapy has a return of cancer cells.

As used herein, and unless otherwise specified, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response" can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

As used herein, and unless otherwise specified, the term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

As used herein, and unless otherwise specified, the term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

As used herein, and unless otherwise specified, the term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking the immunomodulatory compound being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

As used herein, and unless otherwise specified, the term "refractory or resistant" refers to a circumstance where a subject or a mammal, even after intensive treatment, has residual cancer cells in his body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

As used herein, and unless otherwise specified, the terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

As used herein and unless otherwise specified, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. In certain embodiments, a stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, greater than about 70% by weight, or greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Clinical Trial Endpoints for Cancer Approval

"Overall survival" (OS) is defined as the time from first dose until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on cancer assessments. These endpoints include disease free survival (DFS), objective response rate (ORR), time to progression (TTP), progression-free survival (PFS), event-free survival (EFS), duration of response (DOR) and time-to-treatment failure (TTF). The collection and analysis of data on these time-dependent endpoints are based on indirect assessments, calculations, and estimates.

Generally, "disease free survival" (DFS) is defined as the time from randomization until recurrence of cancer or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior cancer progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the sum of the percentage of patients who achieve complete and partial responses. Response duration usually is measured from the time of initial response until documented cancer progression. Generally, the FDA has defined ORR as the sum of partial responses plus complete responses. When defined in this manner, ORR is a direct measure of drug anticancer activity, which can be evaluated in a single-arm study. If available, standardized criteria should be used to ascertain response. A variety of response criteria have been considered appropriate (e.g., RECIST criteria) (Therasse et al., (2000) *J. Natl. Cancer Inst,* 92: 205-16). The significance of ORR is assessed by its magnitude and duration, and the percentage of complete responses (no detectable evidence of cancer).

"Duration of response" (DOR) is the time from achieving a response until relapse or disease progression.

"Time to progression" (TTP) and "progression-free survival" (PFS) have served as primary endpoints for drug approval. TTP is defined as the time from randomization until objective cancer progression; TTP does not include deaths. PFS is defined as the time from randomization until objective cancer progression or death. Compared with TTP, PFS is the preferred regulatory endpoint. PFS includes deaths and thus can be a better correlate to overall survival. PFS assumes patient deaths are randomly related to cancer progression. However, in situations where the majority of deaths are unrelated to cancer, TTP can be an acceptable endpoint.

As an endpoint to support drug approval, PFS can reflect cancer growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Event-free survival" (EFS) is the time from study entry until any treatment failure, including disease progression, treatment discontinuation for any reason, or death.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

In certain embodiments, the methods provided herein are useful for achieving one or more of these clinical trial endpoints in a patient. In certain embodiments, the methods provided herein are useful for improving one or more of these clinical trial endpoints in a patient.

Compounds

In certain embodiments, the compound for use in the compositions and methods provided herein is 3-(4-((4-(morpholinomethyl)benzyl)oxy)-1-oxoisoindolin-2-yl)piperidine-2,6-dione (Compound A), having the following structure:

Compound A

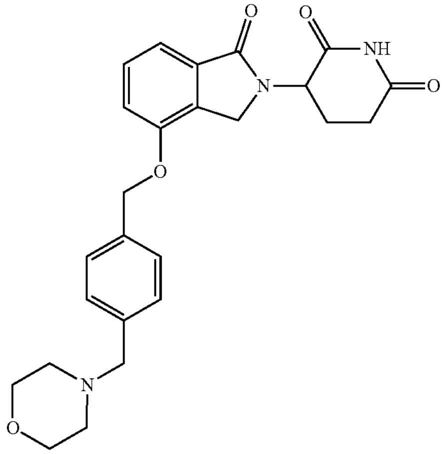

or an enantiomer or a mixture of enantiomers thereof; or a pharmaceutically acceptable salt, solvate, hydrate, co-crystal, clathrate, or polymorph thereof.

In one embodiment, the compound is 3-(4-((4-(morpholinomethyl)benzyl)oxy)-1-oxoisoindolin-2-yl)piperidine-2,6-dione. In one embodiment, the compound is a pharmaceutically acceptable salt of Compound A. In one embodiment, the compound is 3-(4-((4-(morpholinomethyl)benzyl)oxy)-1-oxoisoindolin-2-yl)piperidine-2,6-dione hydrochloride.

In one embodiment, the compound is (S)-3-(4-((4-(morpholinomethyl)benzyl)oxy)-1-oxoisoindolin-2-yl)piperidine-2,6-dione (Compound A-S), having the following structure:

Compound A-S

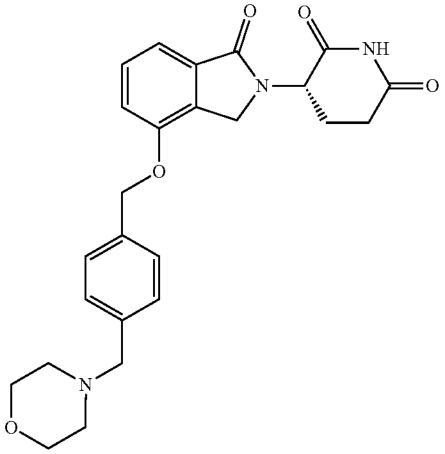

In one embodiment, the compound is a pharmaceutically acceptable salt of Compound A-S. In one embodiment, the compound is (S)-3-(4-((4-(morpholinomethyl)benzyl)oxy)-1-oxoisoindolin-2-yl)piperidine-2,6-dione hydrochloride.

In one embodiment, the compound is (R)-3-(4-((4-(morpholinomethyl)benzyl)oxy)-1-oxoisoindolin-2-yl)piperidine-2,6-dione (Compound A-R), having the following structure:

Compound A-R

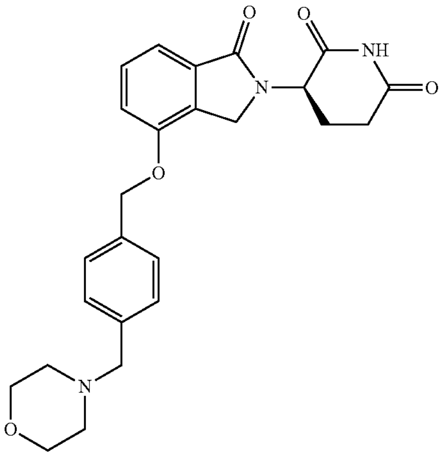

In one embodiment, the compound is a pharmaceutically acceptable salt of compound A-R. In one embodiment, the compound is (R)-3-(4-((4-(morpholinomethyl)benzyl)oxy)-1-oxoisoindolin-2-yl)piperidine-2,6-dione hydrochloride.

Compound A can be prepared according to the methods described in U.S. Application Publication Nos. US2011-0196150 and US2014-0045843, the entirety of each of which is incorporated herein by reference. The compound can be also synthesized according to other methods apparent to those of skill in the art based upon the teaching of these publications.

Compounds provided herein markedly inhibit TNF-α, IL-10, and other inflammatory cytokines in LPS-stimulated hPBMC and human whole blood. TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by the immunomodulatory compounds provided herein is the reduction of synthesis of TNF-α. The immunomodulatory compounds provided herein enhance the degradation of TNF-α mRNA. The compounds provided herein also potently inhibit IL-1 β and stimulates IL-10 under these conditions.

Further, without being limited by any particular theory, the compounds provided herein are potent co-stimulators of T cells and increase cell proliferation in a dose dependent manner under appropriate conditions.

In certain embodiments, without being limited by theory, the biological effects exerted by the immunomodulatory compounds provided herein include, but not limited to, anti-angiogenic and immune modulating effects.

Compound A provided herein contains one chiral center, and can exist as a mixture of enantiomers, e.g., a racemic mixture. This disclosure encompasses the use of stereomerically pure forms of such a compound, as well as the use of mixtures of those forms. For example, mixtures comprising equal or unequal amounts of the enantiomers of Compound A provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of*

*Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN, 1972).

In certain embodiments, the compound for use in the compositions and methods provided herein is (11b,16a)-9-fluoro-11,17,21-trihydroxy-16-methylpregna-1,4-diene-3,20-dione, having the following structure:

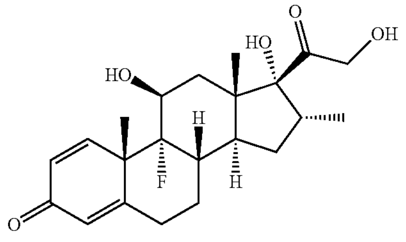

Dexamethasone or an enantiomer or a mixture of enantiomers thereof or a pharmaceutically acceptable salt, solvate, hydrate, co-crystal, clathrate, or polymorph thereof.

In one embodiment, the compound is (11b,16a)-9-fluoro-11,17,21-trihydroxy-16-methylpregna-1,4-diene-3,20-dione. In one embodiment, the compound is a pharmaceutically acceptable salt of dexamethasone. In one embodiment, the compound is dexamethasone sodium phosphate.

Dexamethasone can be prepared according to the methods described in U.S. Pat. Nos. 2,990,401 and 3,035,050, the entirety of each of which is incorporated herein by reference.

In certain embodiments, the compound for use in the compositions and methods provided herein is a monoclonal antibody that binds to CD38. In particular, the anti-CD38 antibody is daratumumab. Daratumumab is approved for the treatment of multiple myeloma.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

Methods of Treatment and Compounds for Use in Such Methods

Provided herein are methods of treating and/or managing cancer, which comprise administering to a patient in need of such treatment and/or management a therapeutically or prophylactically effective amount of 3-(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof, as a part of a combination therapy. Provided herein is 3-(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof for use in such methods of treating and/or managing cancer. In some embodiments, the compound is (S)-3-(4-((4-(morpholinomethyl)benzyl)oxy)-1-oxoisoindolin-2-yl)piperidine-2,6-dione (Compound A-S). In some embodiments, the compound is (R)-3-(4-((4-(morpholinomethyl)benzyl)oxy)-1-oxoisoindolin-2-yl)piperidine-2,6-dione (Compound A-R).

Provided herein are methods of treating and/or managing cancer, which comprise administering to a patient in need of such treatment and/or management a therapeutically or prophylactically effective amount of 3-(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof and daratumumab. Provided herein is 3-(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof for use in such methods. In some embodiments, the compound is (S)-3-(4-((4-(morpholinomethyl)benzyl)oxy)-1-oxoisoindolin-2-yl)piperidine-2,6-dione (Compound A-S). In some embodiments, the compound is (R)-3-(4-((4-(morpholinomethyl)benzyl)oxy)-1-oxoisoindolin-2-yl)piperidine-2,6-dione (Compound A-R).

Provided herein are methods of treating and/or managing cancer, which comprise administering to a patient in need of such treatment and/or management a therapeutically or prophylactically effective amount of 3-(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof, daratumumab and dexamethasone, or an enantiomer or a mixture of enantiomers thereof, or a pharmaceutically acceptable salt, solvate, hydrate, co-crystal, clathrate, or polymorph thereof. Provided herein is -(4-((4-(morpholinomethyl)benzyl)oxy)-1-oxoisoindolin-2-yl)piperidine-2,6-dione (Compound A), or an enantiomer or a mixture of enantiomers thereof, or a pharmaceutically acceptable salt, solvate, hydrate, co-crystal, clathrate, or polymorph thereof for use in such methods of treating and/or managing cancer. In some embodiments, the compound is (S)-3-(4-((4-(morpholinomethyl)benzyl)oxy)-1-oxoisoindolin-2-yl)piperidine-2,6-dione (Compound A-S). In some embodiments, the compound is (R)-3-(4-((4-(morpholinomethyl)benzyl)oxy)-1-oxoisoindolin-2-yl)piperidine-2,6-dione (Compound A-R).

As used herein, the term "cancer" includes, but is not limited to, blood born tumors. In certain embodiments, term "cancer" includes karotype acute myeloblastic leukemia, multiple myeloma, Hodgkin's lymphoma, non-Hodgkin's lymphoma, cutaneous T-Cell lymphoma, cutaneous B-Cell lymphoma, diffuse large B-Cell lymphoma and low grade follicular lymphoma.

In certain embodiments, the cancer is a hematological tumor. In certain embodiments, the hematological tumor is metastatic. In certain embodiments, the hematological tumor is drug resistant. In certain embodiments, the cancer is myeloma or lymphoma. In certain embodiments, the myeloma is multiple myeloma.

In certain embodiments, the multiple myeloma is smoldering myeloma, indolent myeloma, active multiple myeloma, extramedullary plasmacytoma, solitary plasmacytoma of the bone, light chain myeloma, or non-secretory myeloma. In certain embodiments, the multiple myeloma is relapsed, refractory or resistant multiple myeloma. In certain embodiments, the multiple myeloma is relapsed and refractory multiple myeloma.

Provided herein are methods of treating or managing myeloma, particularly multiple myeloma. In some embodiments, provided herein are methods for the treatment or management of smoldering myeloma, indolent myeloma, active multiple myeloma, extramedullary plasmacytoma, solitary plasmacytoma of the bone, light chain myeloma, or non-secretory myeloma. In some embodiments, provided herein are methods for the treatment or management of relapsed, refractory or resistant multiple myeloma. In some embodiments, provided herein are methods for the treatment or management of relapsed and refractory multiple myeloma.

In one embodiment, provided herein are methods for the treatment or management of lymphoma. In certain embodiments, provided herein are methods for the treatment or management of Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

The methods provided herein encompass methods for screening or identifying cancer patients, e.g., multiple myeloma patients, for treatment with Compound A, or an enantiomer or a mixture of enantiomers thereof, or a pharmaceutically acceptable salt, solvate, hydrate, co-crystal, clathrate, or polymorph thereof in combination with daratumumab. In particular, provided herein are methods for selecting patients having, or who are likely to have, a higher response rate to a therapy with Compound A, or an enantiomer or a mixture of enantiomers thereof, or a pharmaceutically acceptable salt, solvate, hydrate, co-crystal, clathrate, or polymorph thereof in combination with daratumumab.

Some methods provided herein encompass methods for screening or identifying cancer patients, e.g., multiple myeloma patients, for treatment with Compound A, or an enantiomer or a mixture of enantiomers thereof, or a pharmaceutically acceptable salt, solvate, hydrate, co-crystal, clathrate, or polymorph thereof in combination with daratumumab and dexamethasone, or an enantiomer or a mixture of enantiomers thereof, or a pharmaceutically acceptable salt, solvate, hydrate, co-crystal, clathrate, or polymorph thereof. In particular, provided herein are methods for selecting patients having, or who are likely to have, a higher response rate to a therapy with Compound A, or an enantiomer or a mixture of enantiomers thereof, or a pharmaceutically acceptable salt, solvate, hydrate, co-crystal, clathrate, or polymorph thereof in combination with daratumumab and dexamethasone, or an enantiomer or a mixture of enantiomers thereof, or a pharmaceutically acceptable salt, solvate, hydrate, co-crystal, clathrate, or polymorph thereof.

Also provided herein is a method for treating or managing multiple myeloma, comprising:

(i) identifying a patient having multiple myeloma sensitive to treatment with (a) Compound A, or an enantiomer or a mixture of enantiomers thereof, or a pharmaceutically acceptable salt, solvate, hydrate, co-crystal, clathrate, or polymorph thereof and (b) daratumumab; and (ii) administering to the patient a therapeutically effective amount of (a) Compound A, or an enantiomer or a mixture of enantiomers thereof, or a pharmaceutically acceptable salt, solvate, hydrate, co-crystal, clathrate, or polymorph thereof and (b) daratumumab.

Provided herein is Compound A, or an enantiomer or a mixture of enantiomers thereof, or a pharmaceutically acceptable salt, solvate, hydrate, co-crystal, clathrate, or polymorph thereof for use in such a method for treating or managing multiple myeloma.

Also provided herein is a method for treating or managing multiple myeloma, comprising:

(i) identifying a patient having multiple myeloma sensitive to treatment with (a) Compound A, or an enantiomer or a mixture of enantiomers thereof, or a pharmaceutically acceptable salt, solvate, hydrate, co-crystal, clathrate, or polymorph thereof, (b) daratumumab and (c) dexamethasone, or an enantiomer or a mixture of enantiomers thereof, or a pharmaceutically acceptable salt, solvate, hydrate, co-crystal, clathrate, or polymorph thereof and (ii) administering to the patient a therapeutically effective amount of (a) Compound A, or an enantiomer or a mixture of enantiomers thereof, or a pharmaceutically acceptable salt, solvate, hydrate, co-crystal, clathrate, or polymorph thereof, (b) daratumumab and (c) dexamethasone, or an enantiomer or a mixture of enantiomers thereof, or a pharmaceutically acceptable salt, solvate, hydrate, co-crystal, clathrate, or polymorph thereof.

Provided herein is Compound A, or an enantiomer or a mixture of enantiomers thereof, or a pharmaceutically acceptable salt, solvate, hydrate, co-crystal, clathrate, or polymorph thereof for use in such a method for treating or managing multiple myeloma.

Provided herein are methods of treating cancer, e.g., multiple myeloma, lymphoma and leukemia, which result in an improvement in overall survival of the patient. In some embodiments, the improvement in overall survival of the patient is observed in a patient population sensitive to treatment with (i) Compound A, or an enantiomer or a mixture of enantiomers thereof, or a pharmaceutically acceptable salt, solvate, hydrate, co-crystal, clathrate, or polymorph thereof and (ii) daratumumab.

Also provided herein are methods of treating cancer, e.g., multiple myeloma, lymphoma and leukemia, which result in an improvement in overall survival of the patient. In some embodiments, the improvement in overall survival of the patient is observed in a patient population sensitive to treatment with (i) Compound A, or an enantiomer or a mixture of enantiomers thereof, or a pharmaceutically acceptable salt, solvate, hydrate, co-crystal, clathrate, or polymorph thereof, (ii) daratumumab and (iii) dexamethasone, or an enantiomer or a mixture of enantiomers thereof, or a pharmaceutically acceptable salt, solvate, hydrate, co-crystal, clathrate, or polymorph thereof.

In other embodiments, provided herein are methods of treating cancer, e.g., multiple myeloma, lymphoma and leukemia, which result in disease free survival of the patient. In some embodiments, disease free survival of the patient is observed in a patient population sensitive to treatment with (i) Compound A, or an enantiomer or a mixture of enantiomers thereof, or a pharmaceutically acceptable salt, solvate, hydrate, co-crystal, clathrate, or polymorph thereof and (ii) daratumumab.

In other embodiments, provided herein are methods of treating cancer, e.g., multiple myeloma, lymphoma and leukemia, which result in disease free survival of the patient. In some embodiments, disease free survival of the patient is observed in a patient population sensitive to treatment with (i) Compound A, or an enantiomer or a mixture of enantiomers thereof, or a pharmaceutically acceptable salt, solvate, hydrate, co-crystal, clathrate, or polymorph thereof, (ii) daratumumab and (iii) dexamethasone, or an enantiomer or a mixture of enantiomers thereof, or a pharmaceutically acceptable salt, solvate, hydrate, co-crystal, clathrate, or polymorph thereof.

In other embodiments, provided herein are methods of treating cancer, e.g., multiple myeloma, lymphoma and leukemia, which result in an improvement in the objective response rate in the patient population. In some embodiments, the patient population sensitive to treatment with (i) Compound A, or an enantiomer or a mixture of enantiomers thereof, or a pharmaceutically acceptable salt, solvate, hydrate, co-crystal, clathrate, or polymorph thereof and (ii) daratumumab.

In other embodiments, provided herein are methods of treating cancer, e.g., multiple myeloma, lymphoma and leukemia, which result in an improvement in the objective response rate in the patient population. In some embodiments, the patient population sensitive to treatment with (i) Compound A, or an enantiomer or a mixture of enantiomers thereof, or a pharmaceutically acceptable salt, solvate, hydrate, co-crystal, clathrate, or polymorph thereof, (ii) daratumumab and (iii) dexamethasone, or an enantiomer or a mixture of enantiomers thereof, or a pharmaceutically acceptable salt, solvate, hydrate, co-crystal, clathrate, or polymorph thereof.

In some embodiments, Compound A, or an enantiomer or a mixture of enantiomers thereof, or a pharmaceutically acceptable salt, solvate, hydrate, co-crystal, clathrate, or polymorph thereof and daratumumab, are administered in combination with a therapy conventionally used to treat or manage cancer. In some embodiments, Compound A, or an enantiomer or a mixture of enantiomers thereof, or a pharmaceutically acceptable salt, solvate, hydrate, co-crystal, clathrate, or polymorph thereof, daratumumab and dexamethasone, or an enantiomer or a mixture of enantiomers thereof, or a pharmaceutically acceptable salt, solvate, hydrate, co-crystal, clathrate, or polymorph thereof, are administered in combination with a therapy conventionally used to treat or manage cancer. Examples of such conventional therapies include, but are not limited to, surgery, chemotherapy, radiation therapy, hormonal therapy, biological therapy and immunotherapy.

In some embodiments, the methods for treating and/or managing multiple myeloma provided herein may be used in patients that have not responded to standard treatment. In one embodiment, the multiple myeloma is relapsed, refractory or resistant to conventional therapy.

In other embodiments, the methods for treating and/or managing multiple myeloma provided herein may be used in treatment naive patients, i.e., patients that have not yet received treatment.

In certain embodiments, Compound A, or an enantiomer or a mixture of enantiomers thereof, or a pharmaceutically acceptable salt, solvate, hydrate, co-crystal, clathrate, or polymorph thereof and daratumumab, are administered in combination or alternation with a therapeutically effective amount of one or more additional active agents. In certain embodiments, Compound A, or an enantiomer or a mixture of enantiomers thereof, or a pharmaceutically acceptable salt, solvate, hydrate, co-crystal, clathrate, or polymorph thereof daratumumab and dexamethasone, or an enantiomer or a mixture of enantiomers thereof, or a pharmaceutically acceptable salt, solvate, hydrate, co-crystal, clathrate, or polymorph thereof, are administered in combination or alternation with a therapeutically effective amount of one or more additional active agents.

Additional active agents include small molecules and large molecules (e.g., proteins and antibodies), examples of which are provided herein, as well as stem cells. Methods or therapies that can be used in combination with the administration of the compounds provided herein include, but are not limited to, surgery, blood transfusions, immunotherapy, biological therapy, radiation therapy, and other non-drug based therapies presently used to treat and/or manage disease and conditions associated with or characterized by undesired angiogenesis.

In one embodiment, the additional active agent is selected from the group consisting of an alkylating agent, an adenosine analog, a glucocorticoid, a kinase inhibitor, a SYK inhibitor, a PDE3 inhibitor, a PDE7 inhibitor, doxorubicin, chlorambucil, vincristine, bendamustine, forskolin, rituximab, or a combination thereof.

In one embodiment, the additional active agent is rituximab. In another embodiment, the additional active agent is prednisone.

Provided herein are methods of treating patients who have been previously treated for cancer but are non-responsive to standard therapies, as well as those who have not previously been treated. Provided herein are methods of treating patients who have been previously treated for multiple myeloma but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

Provided herein are methods of treating patients who have been previously treated for cancer using at least two prior lines of therapy. Also provided herein are methods of treating patients who have been previously treated for multiple myeloma using at least two prior lines of therapy.

In certain embodiments, provided herein are methods of treating and/or managing relapsed/refractory multiple myeloma in patients, comprising administering a therapeutically effective amount of Compound A, or an enantiomer or a mixture of enantiomers thereof, or a pharmaceutically acceptable salt, solvate, hydrate, stereoisomer, tautomer or racemic mixtures thereof in combination with daratumumab, to a patient having relapsed/refractory multiple myeloma. Provided herein is Compound A, or an enantiomer or a mixture of enantiomers thereof, or a pharmaceutically acceptable salt, solvate, hydrate, stereoisomer, tautomer or racemic mixtures thereof for use in such methods of treating and/or managing relapsed/refractory multiple myeloma in patients. In one embodiment, provided herein are methods of treating and/or managing relapsed/refractory multiple myeloma in patients, comprising administering a therapeutically effective amount of Compound A-S or a pharmaceutically acceptable salt thereof in combination with daratumumab, to a patient having relapsed/refractory multiple myeloma. Provided herein is Compound A-S or a pharmaceutically acceptable salt thereof for use in such methods of treating and/or managing relapsed/refractory multiple myeloma in patients.

In certain embodiments, provided herein are methods of treating and/or managing relapsed/refractory multiple myeloma in patients, comprising administering a therapeutically effective amount of Compound A, or an enantiomer or a mixture of enantiomers thereof, or a pharmaceutically acceptable salt, solvate, hydrate, stereoisomer, tautomer or racemic mixtures thereof in combination with daratumumab and dexamethasone, to a patient having relapsed/refractory multiple myeloma. Provided herein is Compound A, or an enantiomer or a mixture of enantiomers thereof, or a pharmaceutically acceptable salt, solvate, hydrate, stereoisomer, tautomer or racemic mixtures thereof for use in such methods of treating and/or managing relapsed/refractory multiple myeloma in patients. In one embodiment, provided herein are methods of treating and/or managing relapsed/refractory multiple myeloma in patients, comprising administering a therapeutically effective amount of Compound A-S or a pharmaceutically acceptable salt thereof in combination with daratumumab and dexamethasone, to a patient having relapsed/refractory multiple myeloma. Provided herein is Compound A-S or a pharmaceutically acceptable salt thereof for use in such methods of treating and/or managing relapsed/refractory multiple myeloma in patients.

In certain embodiments, provided herein are methods for treating and/or managing relapsed/refractory multiple myeloma in patients.

In certain embodiments, a therapeutically or prophylactically effective amount of Compound A is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day. In some embodiments, a therapeutically or prophylactically effective amount of Compound A is from about 0.005 to about 1,000 mg per day. In some embodiments, a therapeutically or prophylactically effective amount of Compound A is from about 0.01 to about 500 mg per day. In some embodiments, a therapeutically or prophylactically effective amount of Compound A is from about 0.01 to about 250 mg per day. In some embodiments, a therapeutically or prophylactically effective amount of Compound A is from about 0.01 to about 100 mg per day. In some embodiments, a therapeutically or prophylactically effective amount of Compound A is from about 0.1 to about 100 mg per day. In some embodiments, a therapeutically or prophylactically effective amount of Compound A is from about 0.5 to about 100 mg per day. In some embodiments, a therapeutically or prophylactically effective amount of Compound A is from about 1 to about 100 mg per day. In some embodiments, a therapeutically or prophylactically effective amount of Compound A is from about 0.01 to about 50 mg per day. In some embodiments, a therapeutically or prophylactically effective amount of Compound A is from about 0.1 to about 50 mg per day. In some embodiments, a therapeutically or prophylactically effective amount of Compound A is from about 0.5 to about 50 mg per day. In some embodiments, a therapeutically or prophylactically effective amount of Compound A is from about 1 to about 50 mg per day. In some embodiments, a therapeutically or prophylactically effective amount of Compound A is from about 0.02 to about 25 mg per day. In some embodiments, a therapeutically or prophylactically effective amount of Compound A is from about 0.05 to about 10 mg per day.

In certain embodiments, the therapeutically or prophylactically effective amount of Compound A is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day. In certain embodiments, the therapeutically or prophylactically effective amount of Compound A is about 0.1 mg per day. In some embodiments, the therapeutically or prophylactically effective amount of Compound A is about 0.2 mg per day. In some embodiments, the therapeutically or prophylactically effective amount of Compound A is about about 0.5 mg per day. In some embodiments, the therapeutically or prophylactically effective amount of Compound A is about about 1 mg per day. In some embodiments, the therapeutically or prophylactically effective amount of Compound A is about about 2 mg per day. In some embodiments, the therapeutically or prophylactically effective amount of Compound A is about about 5 mg per day. In some embodiments, the therapeutically or prophylactically effective amount of Compound A is about about 10 mg per day. In some embodiments, the therapeutically or prophylactically effective amount of Compound A is about about 15 mg per day. In some embodiments, the therapeutically or prophylactically effective amount of Compound A is about about 20 mg per day. In some embodiments, the therapeutically or prophylactically effective amount of Compound A is about about 25 mg per day. In some embodiments, the therapeutically or prophylactically effective amount of Compound A is about about 30 mg per day. In some embodiments, the therapeutically or prophylactically effective amount of Compound A is about about 40 mg per day. In some embodiments, the therapeutically or prophylactically effective amount of Compound A is about about 45 mg per day. In some embodiments, the therapeutically or prophylactically effective amount of Compound A is about about 50 mg per day. In some embodiments, the therapeutically or prophylactically effective amount of Compound A is about about 60 mg per day. In some embodiments, the therapeutically or prophylactically effective amount of Compound A is about about 70 mg per day. In some embodiments, the therapeutically or prophylactically effective amount of Compound A is about about 80 mg per day. In some embodiments, the therapeutically or prophylactically effective amount of Compound A is about about 90 mg per day. In some embodiments, the therapeutically or prophylactically effective amount of Compound A is about about 100 mg per day. In some embodiments, the therapeutically or prophylactically effective amount of Compound A is about about 150 mg per day.

In certain embodiments, a therapeutically or prophylactically effective amount of Compound A-S is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 10 mg per day, from about 0.5 to about 10 mg per day, from about 1 to about 10 mg per day, from about 0.02 to about 5 mg per day, or from about 0.05 to about 5 mg per day. In some embodiments, a therapeutically or prophylactically effective amount of Compound A-S is from about 0.005 to about 1,000 mg per day. In some embodiments, a therapeutically or prophylactically effective amount of Compound A-S is from about 0.01 to about 500 mg per day. In some embodiments, a therapeutically or prophylactically effective amount of Compound A-S is from about 0.01 to about 250 mg per day. In some embodiments, a therapeutically or prophylactically effective amount of Compound A-S is from about 0.01 to about 100 mg per day. In some embodiments, a therapeutically or prophylactically effective amount of Compound A-S is from about 0.1 to about 100 mg per day. In some embodiments, a therapeutically or prophylactically effective amount of Compound A-S is from about 0.5 to about 100 mg per day. In some embodiments, a therapeutically or prophylactically effective amount of Compound A-S is from about 1 to about 100 mg per day. In some embodiments, a therapeutically or prophylactically effective amount of Compound A-S is from about 0.01 to about 50 mg per day. In some embodiments, a therapeutically or prophylactically effective amount of Compound A-S is from about 0.1 to about 10 mg per day. In some embodiments, a therapeutically or prophylactically effective amount of Compound A-S is from about 0.5 to about 10 mg per day. In some embodiments, a therapeutically or prophylactically effective amount of Compound A-S is from about 1 to about 10 mg per day. In some embodiments, a therapeutically or prophylactically effective amount of Compound A-S is from about 0.02 to about 5 mg per day. In some embodiments, a therapeutically or prophylactically effective amount of Compound A-S is from about 0.05 to about 5 mg per day.

In certain embodiments, the therapeutically or prophylactically effective amount of Compound A-S is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day. In some embodiments, the therapeutically or prophylactically effective amount of Compound A-S is about 0.1 mg per day. In some embodiments, the therapeutically or prophylactically effective amount of Compound A-S is about 0.2 mg per day. In some embodiments, the therapeutically or prophylactically effective amount of Compound A-S is about 0.5 mg per day. In some embodiments, the therapeutically or prophylactically effective amount of Compound A-S is about 1 mg per day. In some embodiments, the therapeutically or prophylactically effective amount of Compound A-S is about 2 mg per day. In some embodiments, the therapeutically or prophylactically effective amount of Compound A-S is about 5 mg per day. In some embodiments, the therapeutically or prophylactically effective amount of Compound A-S is about 10 mg per day. In some embodiments, the therapeutically or prophylactically effective amount of Compound A-S is about 15 mg per day. In some embodiments, the therapeutically or prophylactically effective amount of Compound A-S is about 20 mg per day. In some embodiments, the therapeutically or prophylactically effective amount of Compound A-S is about 25 mg per day. In some embodiments, the therapeutically or prophylactically effective amount of Compound A-S is about 30 mg per day. In some embodiments, the therapeutically or prophylactically effective amount of Compound A-S is about 40 mg per day. In some embodiments, the therapeutically or prophylactically effective amount of Compound A-S is about 45 mg per day. In some embodiments, the therapeutically or prophylactically effective amount of Compound A-S is about 50 mg per day. In some embodiments, the therapeutically or prophylactically effective amount of Compound A-S is about 60 mg per day. In some embodiments, the therapeutically or prophylactically effective amount of Compound A-S is about 70, mg per day. In some embodiments, the therapeutically or prophylactically effective amount of Compound A-S is about 80 mg per day. In some embodiments, the therapeutically or prophylactically effective amount of Compound A-S is about 90 mg per day. In some embodiments, the therapeutically or prophylactically effective amount of Compound A-S is about 100 mg per day. In some embodiments, the therapeutically or prophylactically effective amount of Compound A-S is about 150 mg per day.

In certain embodiments, a therapeutically or prophylactically effective amount of Compound A-R is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 10 mg per day, from about 0.5 to about 10 mg per day, from about 1 to about 10 mg per day, from about 0.02 to about 5 mg per day, or from about 0.05 to about 5 mg per day. In some embodiments, a therapeutically or prophylactically effective amount of Compound A-R is from about 0.005 to about 1,000 mg per day. In some embodiments, a therapeutically or prophylactically effective amount of Compound A-R is from about 0.01 to about 500 mg per day. In some embodiments, a therapeutically or prophylactically effective amount of Compound A-R is from about 0.01 to about 250 mg per day. In some embodiments, a therapeutically or prophylactically effective amount of Compound A-R is from about 0.01 to about 100 mg per day. In some embodiments, a therapeutically or prophylactically effective amount of Compound A-R is from about 0.1 to about 100 mg per day. In some embodiments, a therapeutically or prophylactically effective amount of Compound A-R is from about 0.5 to about 100 mg per day. In some embodiments, a therapeutically or prophylactically effective amount of Compound A-R is from about 1 to about 100 mg per day. In some embodiments, a therapeutically or prophylactically effective amount of Compound A-R is from about 0.01 to about 50 mg per day. In some embodiments, a therapeutically or prophylactically effective amount of Compound A-R is from about 0.1 to about 10 mg per day. In some embodiments, a therapeutically or prophylactically effective amount of Compound A-R is from about 0.5 to about 10 mg per day. In some embodiments, a therapeutically or prophylactically effective amount of Compound A-R is from about 1 to about 10 mg per day. In some embodiments, a therapeutically or prophylactically effective amount of Compound A-R is from about 0.02 to about 5 mg per day. In some embodiments, a therapeutically or prophylactically effective amount of Compound A-R is from about 0.05 to about 5 mg per day.

In certain embodiments, the therapeutically or prophylactically effective amount of Compound A-R is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day. In some embodiments, the therapeutically or prophylactically effective amount of Compound A-R is about 0.1 mg per day. In some embodiments, the therapeutically or prophylactically effective amount of Compound A-R is about 0.2 mg per day. In some embodiments, the therapeutically or prophylactically effective amount of Compound A-R is about 0.5 mg per day. In some embodiments, the therapeutically or prophylactically effective amount of Compound A-R is about 1 mg per day. In some embodiments, the therapeutically or prophylactically effective amount of Compound A-R is about 2 mg per day. In some embodiments, the therapeutically or prophylactically effective amount of Compound A-R is about 5 mg per day. In some embodiments, the therapeutically or prophylactically effective amount of Compound A-R is about 10 mg per day. In some embodiments, the therapeutically or prophylactically effective amount of Compound A-R is about 15 mg per day. In some embodiments, the therapeutically or prophylactically effective amount of Compound A-R is about 20 mg per day. In some embodiments, the therapeutically or prophylactically effective amount of Compound A-R is about 25 mg per day. In some embodiments, the therapeutically or prophylactically effective amount of Compound A-R is about 30 mg per day. In some embodiments, the therapeutically or prophylactically effective amount of Compound A-R is about 40 mg per day. In some embodiments, the therapeutically or prophylactically effective amount of Compound A-R is about 45 mg per day. In some embodiments, the therapeutically or prophylactically effective amount of Compound A-R is about 50 mg per day. In some embodiments, the therapeutically or prophylactically effective amount of Compound A-R is about 60 mg per day. In some embodiments, the therapeutically or prophylactically effective amount of Compound A-R is about 70, mg per day. In some embodiments, the therapeutically or prophylactically effective amount of Compound A-R is about 80 mg per day. In some embodiments, the therapeutically or prophylactically effective amount of Compound A-R is about 90 mg per day. In some embodiments, the therapeutically or prophylactically effective amount of Compound A-R is about 100 mg per day. In some embodiments, the therapeutically or prophylactically effective amount of Compound A-R is about 150 mg per day.

In one embodiment, the recommended daily dose range of Compound A, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In one embodiment, the recommended daily dose range of Compound A-S, or an enantiomer or a mixture of enantiomers thereof, or a pharmaceutically acceptable salt, solvate, hydrate, co-crystal, clathrate, or polymorph thereof, for the conditions described herein lie within the range of from about 0.1 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.1 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In one embodiment, the recommended daily dose range of Compound A-R, or an enantiomer or a mixture of enantiomers thereof, or a pharmaceutically acceptable salt, solvate, hydrate, co-crystal, clathrate, or polymorph thereof, for the conditions described herein lie within the range of from about 0.1 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.1 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In certain embodiments, a therapeutically or prophylactically effective amount of daratumumab is from about 0.5 to about 2,000 mg/kg per day, from about 1 to about 1,000 mg/kg per day, from about 1 to about 500 mg/kg per day, from about 1 to about 250 mg/kg per day, from about 5 to about 250 mg/kg per day, from about 7.5 to about 250 mg/kg per day, from about 10 to about 250 mg/kg per day, from about 16 to about 250 mg/kg per day, from about 16 to about 200 mg/kg per day, from about 1 to about 100 mg/kg per day, from about 1 to about 50 mg/kg per day, from about 0.5 to about 25 mg/kg per day, or from about 0.5 to about 10 mg/kg per day. In some embodiments, a therapeutically or prophylactically effective amount of daratumumab is from about 0.5 to about 2,000 mg/kg per day. In some embodiments, a therapeutically or prophylactically effective amount of daratumumab is from about 1 to about 1,000 mg/kg per day. In some embodiments, a therapeutically or prophylactically effective amount of daratumumab is from about 1 to about 500 mg/kg per day. In some embodiments, a therapeutically or prophylactically effective amount of daratumumab is from about 1 to about 250 mg/kg per day. In some embodiments, a therapeutically or prophylactically effective amount of daratumumab is from about 5 to about 250 mg/kg per day. In some embodiments, a therapeutically or prophylactically effective amount of daratumumab is from about 7.5 to about 250 mg/kg per day. In some embodiments, a therapeutically or prophylactically effective amount of daratumumab is from about 10 to about 250 mg/kg per day. In some embodiments, a therapeutically or prophylactically effective amount of daratumumab is from about 16 to about 250 mg/kg per day. In some embodiments, a therapeutically or prophylactically effective amount of daratumumab is from about 16 to about 200 mg/kg per day. In some embodiments, a therapeutically or prophylactically effective amount of daratumumab is from about 1 to about 100 mg/kg per day. In some embodiments, a therapeutically or prophylactically effective amount of daratumumab is from about 1 to about 50 mg/kg per day. In some embodiments, a therapeutically or prophylactically effective amount of daratumumab is from about 0.5 to about 25 mg/kg per day. In some embodiments, a therapeutically or prophylactically effective amount of daratumumab is from about 0.5 to about 10 mg/kg per day.

In certain embodiments, the therapeutically or prophylactically effective amount of daratumumab is about 0.5, about 1, about 2, about 5, about 10, about 15, about 20, about 25, about 30, about 40, about 45, about 50, about 60, about 70, about 80, about 90, about 100, about 150, or about 200 mg/kg per day. In certain embodiments, the therapeutically or prophylactically effective amount is about 0.5, about 1, about 2, about 5, about 10, about 15, about 20, about 25, about 30, about 40, about 45, about 50, about 60, about 70, about 80, about 90, about 100, about 150, or about 200 mg/kg per day. In some embodiments, the therapeutically or prophylactically effective amount of daratumumab is about 0.5 mg/kg per day. In some embodiments, the therapeutically or prophylactically effective amount of daratumumab is about 1 mg/kg per day. In some embodiments, the therapeutically or prophylactically effective amount of daratumumab is about 2 mg/kg per day. In some embodiments, the therapeutically or prophylactically effective amount of daratumumab is about 5 mg/kg per day. In some embodiments, the therapeutically or prophylactically effective amount of daratumumab is about 10 mg/kg per day. In some embodiments, the therapeutically or prophylactically effective amount of daratumumab is about 15 mg/kg per day. In some embodiments, the therapeutically or prophylactically effective amount of daratumumab is about 20 mg/kg per day. In some embodiments, the therapeutically or prophylactically effective amount of daratumumab is about 25 mg/kg per day. In some embodiments, the therapeutically or prophylactically effective amount of daratumumab is about 30 mg/kg per day. In some embodiments, the therapeutically or prophylactically effective amount of daratumumab is about 40 mg/kg per day. In some embodiments, the therapeutically or prophylactically effective amount of daratumumab is about 45 mg/kg per day. In some embodiments, the therapeutically or prophylactically effective amount of daratumumab is about 50 mg/kg per day. In some embodiments, the therapeutically or prophylactically effective amount of daratumumab is about 60 mg/kg per day. In some embodiments, the therapeutically or prophylactically effective amount of daratumumab is about 70 mg/kg per day. In some embodiments, the therapeutically or prophylactically effective amount of daratumumab is about 80 mg/kg per day. In some embodiments, the therapeutically or prophylactically effective amount of daratumumab is about 90 mg/kg per day. In some embodiments, the therapeutically or prophylactically effective amount of daratumumab is about 100 mg/kg per day. In some embodiments, the therapeutically or prophylactically effective amount of daratumumab is about 150 mg/kg per day. In some embodiments, the therapeutically or prophylactically effective amount of daratumumab is about 200 mg/kg per day In one embodiment, the recommended daily dose range of daratumumab lie within the range of from about 0.5 mg/kg to about 100 mg/kg per day, preferably given as a single once-a-day dose, or in divided doses throughout a day. In some embodiments, the dosage ranges from about 1 mg/kg to about 100 mg/kg per day. In other embodiments, the dosage ranges from about 0.5 to about 20 mg/kg per day. Specific doses per day include 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 mg/kg per day.

In certain embodiments, a therapeutically or prophylactically effective amount of daratumumab is from about 0.1 to about 100 mg/kg per day, from about 0.1 to about 50 mg/kg per day, from about 0.1 to about 20 mg/kg per day, from about 0.1 to about 10 mg/kg per day. Specific doses per day include about 0.5, 0.3, 1, or about 3 mg/kg per day. In another embodiment, daratumumab is administered in a dose of 1 mg/kg or more, such as a dose of from 1 to 20 mg/kg, e.g. a dose of from 5 to 20 mg/kg, e.g. a dose of 8 mg/kg. In some embodiments, a therapeutically or prophylactically effective amount of daratumumab is from about 0.1 to about 100 mg/kg per day. In some embodiments, a therapeutically or prophylactically effective amount of daratumumab is from about 0.1 to about 50 mg/kg per day. In some embodiments, a therapeutically or prophylactically effective amount of daratumumab is from about 0.1 to about 20 mg/kg per day. In some embodiments, a therapeutically or prophylactically effective amount of daratumumab is from about 0.1 to about 10 mg/kg per day. Specific doses per day include about 0.5 mg/kg per day. In some embodiments, a specific doses per day includes about 0.3 mg/kg per day. In some embodiments, a specific doses per day includes about 1 mg/kg per day. In some embodiments, a specific doses per day includes about 3 mg/kg per day.

In one embodiment, daratumumab is administered by infusion in a weekly dosage of from 10 to 500 mg/$m^2$, such as of from 200 to 400 mg/$m^2$. Such administration may be repeated, e.g., 1 to 8 times, such as 3 to 5 times. The administration may be performed by continuous infusion over a period of from 2 to 24 hours, such as of from 2 to 12 hours. In one embodiment, daratumumab is administered by slow continuous infusion over a long period, such as more than 24 hours, in order to reduce toxic side effects.

In one embodiment, daratumumab is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months.

In a further embodiment, daratumumab is administered once weekly for 2 to 12 weeks, such as for 3 to 10 weeks, such as for 4 to 8 weeks. In one embodiment, daratumumab is administered by maintenance therapy, such as, e.g., once a week for a period of 6 months or more. In one embodiment, daratumumab is administered by a regimen including one infusion of daratumumab followed by an infusion of daratumumab conjugated to a radioisotope. The regimen may be repeated, e.g., 7 to 9 days later.

As non-limiting examples, treatment according to the present invention may be provided as a daily dosage of daratumumab in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In certain embodiments, a therapeutically or prophylactically effective amount of dexamethasone is from about 0.5 to about 2,000 mg per day, from about 1 to about 1,000 mg per day, from about 1 to about 500 mg per day, from about 1 to about 250 mg per day, from about 5 to about 250 mg per day, from about 7.5 to about 250 mg per day, from about 10 to about 250 mg per day, from about 20 to about 250 mg per day, from about 20 to about 200 mg per day, from about 1 to about 100 mg per day, from about 1 to about 50 mg per day, from about 0.5 to about 25 mg per day, or from about 0.5 to about 10 mg per day. In some embodiments, a therapeutically or prophylactically effective amount of dexamethasone is from about 0.5 to about 2,000 mg per day. In some embodiments, a therapeutically or prophylactically effective amount of dexamethasone is from about 1 to about 1,000 mg per day. In some embodiments, a therapeutically or prophylactically effective amount of dexamethasone is from about 1 to about 500 mg per day. In some embodiments, a therapeutically or prophylactically effective amount of dexamethasone is from about 1 to about 250 mg per day. In some embodiments, a therapeutically or prophylactically effective amount of dexamethasone is from about 5 to about 250 mg per day. In some embodiments, a therapeutically or prophylactically effective amount of dexamethasone is from about 7.5 to about 250 mg per day. In some embodiments, a therapeutically or prophylactically effective amount of dexamethasone is from about 10 to about 250 mg per day. In some embodiments, a therapeutically or prophylactically effective amount of dexamethasone is from about 20 to about 250 mg per day. In some embodiments, a therapeutically or prophylactically effective amount of dexamethasone is from about 20 to about 200 mg per day. In some embodiments, a therapeutically or prophylactically effective amount of dexamethasone is from about 1 to about 100 mg per day. In some embodiments, a therapeutically or prophylactically effective amount of dexamethasone is from about 1 to about 50 mg per day. In some embodiments, a therapeutically or prophylactically effective amount of dexamethasone is from about 0.5 to about 25 mg per day. In some embodiments, a therapeutically or prophylactically effective amount of dexamethasone is from about 0.5 to about 10 mg per day.

In certain embodiments, the therapeutically or prophylactically effective amount of dexamethasone is about 0.5, about 1, about 2, about 5, about 10, about 15, about 20, about 25, about 30, about 40, about 45, about 50, about 60, about 70, about 80, about 90, about 100, about 150, or about 200 mg per day. In some embodiments, the therapeutically or prophylactically effective amount of dexamethasone is about 0.5 mg per day. In some embodiments, the therapeutically or prophylactically effective amount of dexamethasone is about 1 mg per day. In some embodiments, the therapeutically or prophylactically effective amount of dexamethasone is about 2 mg per day. In some embodiments, the therapeutically or prophylactically effective amount of dexamethasone is about 5, mg per day. In some embodiments, the therapeutically or prophylactically effective amount of dexamethasone is about 10 mg per day. In some embodiments, the therapeutically or prophylactically effective amount of dexamethasone is about 15 mg per day. In some embodiments, the therapeutically or prophylactically effective amount of dexamethasone is about 20 mg per day. In some embodiments, the therapeutically or prophylactically effective amount of dexamethasone is about 25 mg per day. In some embodiments, the therapeutically or prophylactically effective amount of dexamethasone is about 30 mg per day. In some embodiments, the therapeutically or prophylactically effective amount of dexamethasone is about 40 mg per day. In some embodiments, the therapeutically or prophylactically effective amount of dexamethasone is about 45 mg per day. In some embodiments, the therapeutically or prophylactically effective amount of dexamethasone is about 50 mg per day. In some embodiments, the therapeutically or prophylactically effective amount of dexamethasone is about 60 mg per day. In some embodiments, the therapeutically or prophylactically effective amount of dexamethasone is about 70 mg per day. In some embodiments, the therapeutically or prophylactically effective amount of dexamethasone is about 80 mg per day. In some embodiments, the therapeutically or prophylactically effective amount of dexamethasone is about 90 mg per day. In some embodiments, the therapeutically or prophylactically effective amount of dexamethasone is about 100 mg per day. In some embodiments, the therapeutically or prophylactically effective amount of dexamethasone is about 150 mg per day. In some embodiments, the therapeutically or prophylactically effective amount of dexamethasone is about 200 mg per day.

In one embodiment, the recommended daily dose range of dexamethasone, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 100 mg per day, preferably given as a single once-a-day dose, or in divided doses throughout a day. In some embodiments, the dosage ranges from about 1 mg to about 100 mg per day. In other embodiments, the dosage ranges from about 0.5 to about 20 mg per day. Specific doses include 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 mg per day.

In certain embodiments, the patient to be treated with one of the methods provided herein has not been treated with anticancer therapy prior to the administration of Compound A, or an enantiomer or a mixture of enantiomers thereof, or a pharmaceutically acceptable salt, solvate, hydrate, co-crystal, clathrate, or polymorph thereof and daratumumab. In certain embodiments, the patient to be treated with one of the methods provided herein has been treated with anticancer therapy prior to the administration of Compound A, or an enantiomer or a mixture of enantiomers thereof, or a pharmaceutically acceptable salt, solvate, hydrate, co-crystal, clathrate, or polymorph thereof and daratumumab. In certain embodiments, the patient to be treated with one of the methods provided herein has developed drug resistance to the anticancer therapy.

In certain embodiments, the patient to be treated with one of the methods provided herein has not been treated with anticancer therapy prior to the administration of Compound A, or an enantiomer or a mixture of enantiomers thereof, or a pharmaceutically acceptable salt, solvate, hydrate, co-crystal, clathrate, or polymorph thereof, daratumumab and dexamethasone, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has been treated with anticancer therapy prior to the administration of Compound A, or an enantiomer or a mixture of enantiomers thereof, or a pharmaceutically acceptable salt, solvate, hydrate, co-crystal, clathrate, or polymorph thereof, daratumumab and dexamethasone, or an enantiomer or a mixture of enantiomers thereof, or a pharmaceutically acceptable salt, solvate, hydrate, co-crystal, clathrate, or polymorph thereof. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Compound A, or an enantiomer or a mixture of enantiomers thereof, or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound A, or an enantiomer or a mixture of enantiomers thereof; or a pharmaceutically acceptable salt, solvate, hydrate, co-crystal, clathrate, or polymorph thereof, may be formulated alone or together, in suitable dosage unit with pharmaceutically acceptable excipients, carriers, adjuvants and vehicles, appropriate for each route of administration.

In one embodiment, Compound A, or an enantiomer or a mixture of enantiomers thereof, or a pharmaceutically acceptable salt, solvate, hydrate, co-crystal, clathrate, or polymorph thereof, is administered orally. In another embodiment, Compound A, or an enantiomer or a mixture of enantiomers thereof; or a pharmaceutically acceptable salt, solvate, hydrate, co-crystal, clathrate, or polymorph thereof, is administered parenterally. In yet another embodiment, Compound A, or an enantiomer or a mixture of enantiomers thereof, or a pharmaceutically acceptable salt, solvate, hydrate, co-crystal, clathrate, or polymorph thereof, is administered intravenously.

Compound A, or an enantiomer or a mixture of enantiomers thereof, or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. Compound A, or an enantiomer or a mixture of enantiomers thereof, or a pharmaceutically acceptable salt, solvate, hydrate, co-crystal, clathrate, or polymorph thereof, and daratumumab can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound A, or an enantiomer or a mixture of enantiomers thereof, or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. Compound A, or an enantiomer or a mixture of enantiomers thereof, or a pharmaceutically acceptable salt, solvate, hydrate, co-crystal, clathrate, or polymorph thereof, daratumumab, and dexamethasone, or an enantiomer or a mixture of enantiomers thereof, or a pharmaceutically acceptable salt, solvate, hydrate, co-crystal, clathrate, or polymorph thereof, can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MM scan and other commonly accepted evaluation modalities.

Compound A, or an enantiomer or a mixture of enantiomers thereof, or a pharmaceutically acceptable salt, solvate, hydrate, co-crystal, clathrate, or polymorph thereof, daratumumab or dexamethasone, or an enantiomer or a mixture of enantiomers thereof, or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug).

As used herein, the term "daily" is intended to mean that a therapeutic compound, such as Compound A, is administered once or more than once each day, for example, for a period of time. The term "continuous" is intended to mean that a therapeutic compound, such as Compound A, is administered daily for an uninterrupted period of at least 10 days to 52 weeks. The term "intermittent" or "intermittently" as used herein is intended to mean stopping and starting at either regular or irregular intervals. For example, intermittent administration of Compound A is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound A, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks.

In one embodiment, Compound A, or an enantiomer or a mixture of enantiomers thereof; or a pharmaceutically acceptable salt, solvate, hydrate, co-crystal, clathrate, or polymorph thereof, is administered once a day. In another embodiment, Compound A, or an enantiomer or a mixture of enantiomers thereof; or a pharmaceutically acceptable salt, solvate, hydrate, co-crystal, clathrate, or polymorph thereof, is administered twice a day. In yet another embodiment, Compound A, or an enantiomer or a mixture of enantiomers thereof; or a pharmaceutically acceptable salt, solvate, hydrate, co-crystal, clathrate, or polymorph thereof, is administered three times a day. In still another embodiment, Compound A, or an enantiomer or a mixture of enantiomers thereof; or a pharmaceutically acceptable salt, solvate, hydrate, co-crystal, clathrate, or polymorph thereof, is administered four times a day.

In one embodiment, daratumumab is administered once a day. In another embodiment, daratumumab is administered twice a day. In yet another embodiment, daratumumab is administered three times a day. In still another embodiment, daratumumab is administered four times a day.

In one embodiment, dexamethasone, or an enantiomer or a mixture of enantiomers thereof; or a pharmaceutically acceptable salt, solvate, hydrate, co-crystal, clathrate, or polymorph thereof, is administered once a day. In another embodiment, dexamethasone, or an enantiomer or a mixture of enantiomers thereof; or a pharmaceutically acceptable salt, solvate, hydrate, co-crystal, clathrate, or polymorph thereof, is administered twice a day. In yet another embodiment, dexamethasone, or an enantiomer or a mixture of enantiomers thereof; or a pharmaceutically acceptable salt, solvate, hydrate, co-crystal, clathrate, or polymorph thereof, is administered three times a day. In still another embodiment, dexamethasone, or an enantiomer or a mixture of enantiomers thereof; or a pharmaceutically acceptable salt, solvate, hydrate, co-crystal, clathrate, or polymorph thereof, is administered four times a day.

In certain embodiments, Compound A, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, Compound A, or a pharmaceutically acceptable salt or solvate thereof, is administered once per day for one week, two weeks, three weeks, or four weeks. In one embodiment, Compound A or an enantiomer or a mixture of enantiomers thereof; or a pharmaceutically acceptable salt, solvate, hydrate, co-crystal, clathrate, or polymorph thereof, is administered once per day for one week. In another embodiment, Compound A, or an enantiomer or a mixture of enantiomers thereof; or a pharmaceutically acceptable salt, solvate, hydrate, co-crystal, clathrate, or polymorph thereof, is administered once per day for two weeks. In yet another embodiment, Compound A, or an enantiomer or a mixture of enantiomers thereof; or a pharmaceutically acceptable salt, solvate, hydrate, co-crystal, clathrate, or polymorph thereof, is administered once per day for three weeks. In still another embodiment, Compound A, or an enantiomer or a mixture of enantiomers thereof; or a pharmaceutically acceptable salt, solvate, hydrate, co-crystal, clathrate, or polymorph thereof, is administered once per day for four weeks.

In certain embodiments, Compound A, or an enantiomer or a mixture of enantiomers thereof; or a pharmaceutically acceptable salt, solvate, hydrate, co-crystal, clathrate, or polymorph thereof, is administered once per day for 21 days in each 28 day cycle. In certain embodiments, Compound A, or an enantiomer or a mixture of enantiomers thereof; or a pharmaceutically acceptable salt, solvate, hydrate, co-crystal, clathrate, or polymorph thereof, is administered for one cycle. In certain embodiments, Compound A, or an enantiomer or a mixture of enantiomers thereof; or a pharmaceutically acceptable salt, solvate, hydrate, co-crystal, clathrate, or polymorph thereof, is administered for two cycles. In certain embodiments, Compound A, or an enantiomer or a mixture of enantiomers thereof; or a pharmaceutically acceptable salt, solvate, hydrate, co-crystal, clathrate, or polymorph thereof, is administered for three cycles. In certain embodiments, Compound A, or an enantiomer or a mixture of enantiomers thereof; or a pharmaceutically acceptable salt, solvate, hydrate, co-crystal, clathrate, or polymorph thereof, is administered for four cycles. In certain embodiments, Compound A, or an enantiomer or a mixture of enantiomers thereof; or a pharmaceutically acceptable salt, solvate, hydrate, co-crystal, clathrate, or polymorph thereof, is administered for seven or more cycles.

In certain embodiments, daratumumab is administered once per day on days 1, 8, 15, and 22, in each 28 day cycle. In certain embodiments, daratumumab is administered for one cycle. In certain embodiments, daratumumab is administered for two cycles. In certain embodiments, daratumumab is administered once per day on days 1 and 15 in each 28 day cycle. In certain embodiments, daratumumab is administered for one cycle. In certain embodiments, daratumumab is administered for two cycles. In certain embodiments, daratumumab is administered for three cycles. In certain embodiments, daratumumab is administered for four cycles. In certain embodiments, daratumumab is administered once per day on day 1 in each 28 day cycle. In certain embodiments, daratumumab is administered for seven or more cycles.

In certain embodiments, dexamethasone, or an enantiomer or a mixture of enantiomers thereof; or a pharmaceutically acceptable salt, solvate, hydrate, co-crystal, clathrate, or polymorph thereof, is administered once per day on days 1, 8, 15, and 22, in each 28 day cycle. In certain embodiments, dexamethasone, or an enantiomer or a mixture of enantiomers thereof; or a pharmaceutically acceptable salt, solvate, hydrate, co-crystal, clathrate, or polymorph thereof, is administered for one cycle. In certain embodiments, dexamethasone, or an enantiomer or a mixture of enantiomers thereof; or a pharmaceutically acceptable salt, solvate, hydrate, co-crystal, clathrate, or polymorph thereof, is administered for two cycles. In certain embodiments, dexamethasone, or an enantiomer or a mixture of enantiomers thereof; or a pharmaceutically acceptable salt, solvate, hydrate, co-crystal, clathrate, or polymorph thereof, is administered for three cycles. In certain embodiments, dexamethasone, or an enantiomer or a mixture of enantiomers thereof; or a pharmaceutically acceptable salt, solvate, hydrate, co-crystal, clathrate, or polymorph thereof, is administered for four or more cycles.

Pharmaceutical Compositions and Dosage Forms

In one embodiment, provided herein are pharmaceutical compositions and dosage forms, which comprise (i) Compound A, or an enantiomer or a mixture of enantiomers thereof, or a pharmaceutically acceptable salt, solvate, hydrate, co-crystal, clathrate, or polymorph thereof, and (ii) daratumumab. In another embodiment, pharmaceutical compositions and dosage forms further comprise one or more excipients.

In one embodiment, provided herein are pharmaceutical compositions and dosage forms, which comprise (i) Compound A, or an enantiomer or a mixture of enantiomers thereof, or a pharmaceutically acceptable salt, solvate, hydrate, co-crystal, clathrate, or polymorph thereof, (ii) daratumumab and (iii) dexamethasone. In another embodiment, pharmaceutical compositions and dosage forms further comprise one or more excipients.

In certain embodiments, pharmaceutical compositions and dosage forms provided herein also comprise one or more additional active agents in amounts effective for achieving a modulation of disease or disease symptoms, including those described herein. Examples of optional additional active agents are disclosed herein (see, e.g., definitions section).

In certain embodiments, the pharmaceutical compositions provided herein may be administered orally, parenterally, by inhalation spray, topically, rectally, nasally, buccally, vaginally or via an implanted reservoir, preferably by oral administration or administration by injection. Oral delivery formats include, but are not limited to, tablets, capsules, caplets, solutions, suspensions, and syrups, and may also comprise a plurality of granules, beads, powders or pellets that may or may not be encapsulated. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In certain embodiments, dosage forms provided herein for Compound A, or an enantiomer or a mixture of enantiomers thereof, or a pharmaceutically acceptable salt, solvate, hydrate, co-crystal, clathrate, or polymorph thereof, are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal, or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

In one embodiment, daratumumab is formulated as described in the package insert for DARZALEX®. As described therein, DARZALEX® is injected intravenously. DARZALEX® is available as a solution, at 100 mg/5 ml or 400 mg/20 ml, in a single-dose vial. Each DARZALEX® single dose vial contains glacial acetic acid, mannitol, polysorbate, sodium acetate trihydrate, sodium chloride and water, in addition to daratumumab. The single-dose vial is diluted and DARZALEX® solution administered as an intravenous infusion. For the first infusion DARZALEX® is diluted with 1000 ml of 0.9% Sodium Chloride. For second and subsequent infusions, DARZALEX® is diluted with 500 ml of 0.9% Sodium Chloride, unless there were Grade 1 (mild) or greater infusion reactions during the first infusion, in which case DARZALEX® is diluted with 1000 ml of 0.9% Sodium Chloride.

In one embodiment, provided herein dexamethasone is administered orally or parenterally. In one embodiment, dexamethasone is provided herein as a tablet. In one embodiment, the dexamethasone tablet contains calcium phosphate, lactose, magnesium stearate, and starch. In one embodiment, the dexamethasone tablet is 0.5 mg potency. In one embodiment, the dexamethasone tablet is 0.75 mg potency.

In another embodiment, dexamethasone sodium phosphate is formulated as described in the package insert for HEXADROL® phosphate. As described therein, HEXADROL® phosphate is formulated for injection (intravenous or intramuscular) as a solution at 4 mg/ml. The solution contains sodium sulfite and benzyl alcohol, and is made isotonic with sodium citrate. The pH is adjusted with citric acid or sodium hydroxide to 7.0-8.5.

Whether a particular excipient is suitable for incorporation into a pharmaceutical composition or dosage form provided herein depends on a variety of factors, including, but not limited to, the route of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, encompassed herein are pharmaceutical compositions and dosage forms that contain little, if any, lactose. As used herein, the term "lactose-free" means that the amount of lactose present, if any, is insufficient to substantially increase the degradation rate of an active ingredient.

Lactose-free compositions provided herein can comprise excipients that are listed, for example, in the *U.S. Pharmacopeia* (USP) 25-NF20 (2002). In certain embodiments, lactose-free compositions comprise active ingredients, a binder/filler, and a lubricant in pharmaceutically compatible and pharmaceutically acceptable amounts. In certain embodiments, lactose-free dosage forms comprise active ingredients, microcrystalline cellulose, pre-gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, in certain embodiments, provided herein are anhydrous compositions packaged using materials to prevent exposure to water such that they can be included in suitable formulary kits. Examples of suitable packaging include, but are not limited to, hermetically sealed foils, plastics, unit dose containers (e.g., vials), blister packs, and strip packs.

Encompassed herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Oral Dosage Forms

In certain embodiments, pharmaceutical compositions provided herein that are suitable for oral administration are formulated as discrete dosage forms, examples of which include, but are not limited to, tablets (e.g., chewable tablets), caplets, capsules, and liquids (e.g., flavored syrups). Such dosage forms contain predetermined amounts of active ingredients and may be prepared by some known methods of pharmacy. See generally, *Remington's Pharmaceutical Sciences,* 18th ed., Mack Publishing, Easton PA (1990).

In certain embodiments, the oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms may be prepared by some known methods of pharmacy. In certain embodiments, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet is prepared by compression or molding. In certain embodiments, compressed tablets are be prepared by compressing in a suitable machine the active ingredients in a free-flowing form, e.g., powder or granules, optionally mixed with an excipient. In certain embodiments, molded tablets are made by molding in a suitable machine a mixture of a powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pregelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, AVICEL-PH-101, AVICEL-PH-103 AVICEL RC-581, AVICEL-PH-105 (FMC Corporation, American Viscose Division, Avicel Sales, Marcus Hook, PA), and mixtures thereof. An specific binder is a mixture of microcrystalline cellulose and sodium carboxymethyl cellulose (e.g., AVICEL RC-581). Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein is present in from about 50 to about 99 weight percent of the pharmaceutical composition or dosage form.

Disintegrants are used in the compositions provided herein to provide tablets the ability to disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation. In certain embodiments, the pharmaceutical compositions provided herein comprise from about 0.5 to about 15 weight percent or from about 1 to about 5 weight percent of disintegrant.

Disintegrants that are suitable for use in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that are suitable for use in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, but are not limited to, a syloid silica gel (AEROSIL200, W.R. Grace Co., Baltimore, MD), a coagulated aerosol of synthetic silica (Degussa Co. of Plano, TX), CAB-O-SIL (a pyrogenic silicon dioxide, Cabot Co. of Boston, MA), and mixtures thereof. In certain embodiments, if used at all, lubricants are used in an amount of less than about 1 weight percent of the pharmaceutical compositions or dosage forms into which they are incorporated.

In certain embodiments, provided herein is a solid oral dosage form, comprising Compound A, or an enantiomer or a mixture of enantiomers thereof, or a pharmaceutically acceptable salt, solvate, hydrate, co-crystal, clathrate, or polymorph thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising Compound A, or an enantiomer or a mixture of enantiomers thereof, or a pharmaceutically acceptable salt, solvate, hydrate, co-crystal, clathrate, or polymorph thereof; and anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride salt of Compound A, or an enantiomer or a mixture of enantiomers thereof, or a pharmaceutically solvate, hydrate, co-crystal, clathrate, or polymorph thereof; and one or more excipients selected from anhydrous lactose, microcrystalline cellulose, polyvinylpyrrolidone, stearic acid, colloidal anhydrous silica, and gelatin.

In certain embodiments, provided herein is a solid oral dosage form, comprising a hydrochloride salt of Compound A, or an enantiomer or a mixture of enantiomers thereof, or a pharmaceutically solvate, hydrate, co-crystal, clathrate, or polymorph thereof; and anhydrous lactose, microcrystalline cellulose, polyvinylpyrrolidone, stearic acid, colloidal anhydrous silica, and gelatin.

Delayed Release Dosage Forms

In certain embodiments, the active ingredients provided herein are administered by controlled release means or by delivery devices. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated herein by reference in its entirety. In certain embodiments, such dosage forms are be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Encompassed herein are single unit dosage forms suitable for oral administration, including, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Some suitable vehicles that can be used to provide parenteral dosage forms provided herein include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of Compound A, or an enantiomer or a mixture of enantiomers thereof, or a pharmaceutically acceptable salt, solvate, hydrate, co-crystal, clathrate, or polymorph thereof. See, e.g., U.S. Pat. No. 5,134,127, the disclosure of which is incorporated herein by reference in its entirety.

Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* $16^{th}$ and $18^{th}$ eds., Mack Publishing, Easton PA (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein depend on the particular tissue to which a given pharmaceutical composition or dosage form will be applied. With that fact in mind, in certain embodiments, the excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Additional examples of such ingredients can be found, e.g., in *Remington's Pharmaceutical Sciences,* $16^{th}$ and $18^{th}$ eds., Mack Publishing, Easton PA (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

In certain embodiments, active ingredients provided herein are not administered to a patient at the same time or by the same route of administration. Therefore, encompassed herein are kits which, when used by the medical practitioner, can simplify the administration of appropriate amounts of active ingredients to a patient.

In certain embodiments, a kit provided herein comprises a dosage form of a Compound A, or an enantiomer or a mixture of enantiomers thereof, or a pharmaceutically acceptable salt, solvate, hydrate, co-crystal, clathrate, or polymorph thereof. In certain embodiments, the kits provided herein further comprise dexamethasone and/or daratumumab. In certain embodiments, the kit provided herein further comprises additional active ingredient(s) include, but are not limited to, those disclosed herein.

In certain embodiments, the kit provided herein further comprises a device that is used to administer the active ingredients. Examples of such devices include, but are not limited to, syringes, drip bags, patches, and inhalers.

In certain embodiments, the kit provided herein further comprises cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Certain embodiments of the invention are illustrated by the following non-limiting examples.

Example 1: A Phase 1B/2A Multicenter, Open-Label, Dose Escalation Study to Determine the Maximum Tolerated Dose, Assess the Safety and Tolerability, Pharmacokinetics and Preliminary Efficacy of Compound A-S Monotherapy, in Combination with Dexamethasone, and in Combination with Dexamethasone and Daratumumab in Subjects with Relapsed and Refractory Multiple Myeloma This study will look at the determination of MTD/RP2D, safety and preliminary efficacy measured by overall response rate (ORR), progression-free survival (PFS), and overall survival (OS) in subjects, with relapsed and refractory multiple myeloma after at least two prior lines of therapy, who take (S)-3-(4-((4-(morpholinomethyl)benzyl)oxy)-1-oxoisoindolin-2-yl)piperidine-2,6-dione ("Compound A-S"), in combination with daratumumab and dexamethasone. The study will include a dose escalation phase (Part 1).

This is a phase 1b/2a, multicenter, open label, dose escalation study of the combination of Compound A-S, daratumumab and dexamethasone in subjects with relapsed and refractory multiple myeloma after at least two prior lines of therapy. The primary objective of the study is to determine the maximum tolerated dose (MTD) and/or the recommended Phase 2 dose (RP2D) of Compound A-S when administered with daratumumab and dexamethasone. the study will include a dose escalation phase.

Dose Level(s):

During dose escalation, subjects will be administered Compound A-S orally once daily (QD) for 21 days, combined with daratumumab intravenously (IV), on days 1, 8, 15 and 22 during each 28-day treatment cycle for cycles 1-2; on days 1 and 15 for cycles 3-6; and on day 1 for 7 or more cycles, and with dexamethasone orally on days 1, 8, 15, and 22 of each cycle. Dose escalation will be conducted according to a standard 3+3 dose escalation scheme.

The dose of daratumumab (16 mg/kg) to be used in this study was based on current daratumumab label (Darzalex SmPC, 2017; Darzalex® package insert, 2017). The dose of dexamethasone to be used in this study is 20 mg for subjects >75 years of age and 40 mg for subjects ≤75 years of age.

In Part 1, Compound A-S will start at 0.9 mg QD in combination with daratumumab/dexamethasone and escalate in 0.1 mg increments until the MTD/RP2D is reached or to a maximum of 1.1 mg QD following a standard 3+3 escalation scheme (dose de-escalation to 0.75 mg may occur if needed). Dose levels above 1.1 mg may be tested depending on the RP2D determined.

Escalation to the next higher dose level will be determined by the Dose Escalation Committee (DEC) that includes an independent expert reviewer.

Primary Objectives:

To determine the maximum tolerated dose (MTD) and/or recommended phase 2 dose (RP2D) of Compound A-S when administered in combination with daratumumab and dexamethasone, in subjects with RRMM.

Secondary Objectives:

(1) To evaluate the safety and tolerability of Compound A-S when administered in combination with daratumumab and dexamethasone, in subjects with RRMM. (2) To estimate preliminary efficacy of Compound A-S when administered in combination with daratumumab and dexamethasone, in subjects with RRMM. (3) To evaluate the pharmacokinetics (PK) of Compound A-S when administered in combination with daratumumab and dexamethasone, in subjects with RRMM.

The treatment with investigational product will be continued until progressive disease (PD), unacceptable toxicity or the subject withdraws consent.

The MTD may be the RP2D. The RP2D may also be determined by PK and biomarker data as well as the safety and preliminary efficacy data from Part 1, as applicable. The decision to determine the RP2D will be made in consultation with the DEC.

During the dose-escalation phase, the decision to evaluate subsequent dose levels will be considered and documented by the DEC based on their review of clinical and laboratory safety data for all subjects. Additional dose levels may explored based on the DEC's evaluation and recommendation.

All subjects with a minimal response (MR) or better who discontinue study treatment in Part 1 of the study for a reason other than PD or withdrawal of consent from the study will be followed for response assessment every 28 days until PD or until a subsequent myeloma regimen has been started.

Number of Subjects:

During Part 1, dose escalation will be conducted according to a standard 3+3 dose escalation schema, there will be approximately 36 subjects. The total number of subjects depends on the number of dose levels needed to establish the MTD and/or RP2D and may exceed this approximation.

Study Population:

Eligible subjects must have a documented diagnosis of RRMM. All subjects must have received at least two prior myeloma regimens including lenalidomide or pomalidomide and a proteasome inhibitor and must have been refractory to their last myeloma regimen.

Length of Study:

The study will consist of the Screening and Treatment phases. The Screening phase of this study may not exceed a 28-day window prior to the start of investigational product (Cycle 1 Day 1). This is followed by the Treatment phase consisting of 28-day cycles. Treatment at each dose level and in each part of the study will continue until PD, unacceptable toxicity or the subject withdraws consent. There will be an End of Treatment (EOT) Visit to collect safety and efficacy assessments. There will be a 28-day post-treatment visit to obtain safety assessments.

All subjects with a response of MR (minimal response) or better who discontinue study treatment in Part 1 of the study for a reason other than PD will enter the Post Treatment Response Follow Up phase and will be followed for response assessment every 28 days until PD or a subsequent myeloma regimen has been started.

The End of Trial is defined as either the date of the last long-term follow-up data collection, or the date of receipt of the last data point from the last subject that is required for primary or secondary analysis, whichever is the later date.

Criteria for Inclusion:

(1) Subject must be age 18 years or older at the time of signing the informed consent form (ICF).

(2) Subject must understand and voluntarily sign an ICF prior to any study-related assessments/procedures being conducted.

(3) Subject must be willing and able to adhere to the study visit schedule and other protocol requirements.

(4) Subjects must have a documented diagnosis of MM and have measurable disease defined as: (a) M-protein (serum and/or urine protein electrophoresis (sPEP or uPEP)): sPEP≥0.5 g/dL or uPEP≥200 mg/24 hours and/or (b) Light chain MM without measurable disease in the serum or urine: serum immunoglobulin free light chain ≥10 mg/dL (100 mg/L) and abnormal serum immunoglobulin kappa lambda free light chain ratio.

(5) Subjects must have received at least 2 prior myeloma regimens (note: induction with or without bone marrow transplant and with or without maintenance therapy is considered one regimen).

(6) All subjects must have received prior treatment with at least 2 consecutive cycles of a lenalidomide or pomalidomide-containing regimen.

(7) All subjects must have received prior treatment with at least 2 consecutive cycles of a proteasome inhibitor or a proteasome inhibitor-containing regimen.

(8) All subjects must have documented disease progression on or within 60 days from the last dose of their last myeloma therapy.

(9) All subjects must have Eastern Cooperative Oncology Group (ECOG) performance status score of 0, 1 or 2.

(10) A female of childbearing potential (FCBP) is a female who: 1) has achieved menarche at some point, 2) has not undergone a hysterectomy or bilateral oophorectomy, or 3) has not been naturally postmenopausal (amenorrhea following cancer therapy does not rule out childbearing potential) for at least 24 consecutive months (i.e., has had menses at any time in the preceding 24 consecutive months) and must:

a. Have two negative pregnancy tests as verified by the Investigator prior to starting study treatment. She must agree to ongoing pregnancy testing during the course of the study, and after end of study treatment. This applies even if the subject practices true abstinence from heterosexual contact b. Either commit to true abstinence from heterosexual contact (which must be reviewed on a monthly basis and source documented) or agree to use, and be able to comply with two forms of contraception: one highly effective, and one additional effective (barrier) measure of contraception without interruption 28 days prior to starting investigational product, during the study treatment (including dose interruptions), and for at least 28 days after the last dose of Compound A-S or 90 days after the last dose of daratumumab, whichever is longer.

(11) Male subjects must:

a. Practice true abstinence (which must be reviewed on a monthly basis and source documented) or agree to use a condom during sexual contact with a pregnant female or a female of childbearing potential while participating in the study, during dose interruptions and for at least 90 days following the last dose of study treatment, even if he has undergone a successful vasectomy.

Males must agree to refrain from donating sperm while on study treatment, during dose interruptions and for at least 90 days following last dose of study treatment.

All subjects must agree to refrain from donating blood while on study treatment, during dose interruptions and for at least 28 days following the last dose of study treatment.

All male and female subjects must follow all requirements defined in the Pregnancy Prevention Program.

Exclusion Criteria:

The presence of any of the following will exclude a subject from enrollment:

(1) Subject has any significant medical condition, laboratory abnormality, or psychiatric illness that would prevent the subject from participating in the study.

(2) Subject has any condition including the presence of laboratory abnormalities, which places the subject at unacceptable risk if he/she were to participate in the study.

(3) Subject has any condition that confounds the ability to interpret data from the study.

(4) Subject has nonsecretory or oligosecretory multiple myeloma.

(5) Subjects with Plasma Cell leukemia or amyloidosis.

(6) Any of the following laboratory abnormalities

Absolute neutrophil count (ANC)<1,000/μL

Platelet count <75,000/μL

Corrected serum calcium >13.5 mg/dL (>3.4 mmol/L)

Serum glutamic oxaloacetic transaminase (SGOT)/aspartate aminotransferase (AST) or serum glutamic pyruvic transaminase (SGPT)/alanine aminotransferase (ALT)

≥2.0× upper limit of normal (ULN)

Serum total bilirubin and alkaline phosphatase >1.5× ULN

Subjects with serious renal impairment ([CrCl]<50 mL/min) or requiring dialysis would be excluded (7) Subjects with peripheral neuropathy ≥Grade 2.

(8) Subjects with gastrointestinal disease that may significantly alter the absorption of Compound A-S.

(9) Subjects with a prior history of malignancies, other than MM, unless the subject has been free of the disease for ≥5 years with the exception of the following noninvasive malignancies:

Basal cell carcinoma of the skin

Squamous cell carcinoma of the skin

Carcinoma in situ of the cervix

Carcinoma in situ of the breast

Incidental histological findings of prostate cancer such as T1a or T1b using the Tumor/Node/Metastasis (TNM) classification of malignant tumors or prostate cancer that is curative

(10) Subject has a history of anaphylaxis or hypersensitivity to thalidomide, lenalidomide, pomalidomide, dexamethasone, or daratumumab.

(11) Subject has known or suspected hypersensitivity to the excipients contained in the formulation of Compound A-S, dexamethasone, or daratumumab.

(12) Subject has received any of the following within the last 14 days of initiating investigational product:

Plasmapheresis

Major surgery (as defined by the Investigator)

Radiation therapy other than local therapy for MM associated bone lesions

Use of any systemic myeloma drug therapy

(13) Subject has been treated with an investigational agent (ie, an agent not commercially available) within 28 days or 5 half-lives (whichever is longer) of initiating investigational product.

(14) Subject has any one of the following:

Clinically significant abnormal electrocardiogram (ECG) finding at Screening

Congestive heart failure (New York Heart Association Class III or IV)

Myocardial infarction within 12 months prior to starting investigational product Unstable or poorly controlled angina pectoris, including the Prinzmetal variant of angina pectoris

(15) Subject has current or prior use of immunosuppressive medication within 14 days prior to the first dose of IP. The following are exceptions to this criterion:

Intranasal, inhaled, topical or local steroid injections (eg, intra-articular injection)

Systemic corticosteroids at physiologic doses that do not exceed 10 mg/day of prednisone or equivalent Steroids as premedication for hypersensitivity reactions (eg, computed tomography [CT] scan premedication)

(16) Subject has taken a strong inhibitor or inducer of CYP3A4/5 including grapefruit, St. John's Wort or related products within two weeks prior to dosing and during the course of study.

(17) Subject known to test positive for human immunodeficiency virus (HIV), chronic or active hepatitis B, or active hepatitis A or C.

(18) Subject is unable or unwilling to undergo protocol required thromboembolism prophylaxis.

(19) Subject is a female who is pregnant, nursing or breastfeeding, or who intends to become pregnant during the participation in the study.

(20) Subject has known chronic obstructive pulmonary disease (COPD) with a forced expiratory volume in 1 second (FEV1) 50% of predicted normal. Note that forced expiratory testing (FEV1) is required for subjects suspected of having COPD and subjects must be excluded if FEV1 is <50% of predicted normal.

(21) Subject has received previous allogeneic stem cell transplant; or received autologous stem cell transplantation within 12 weeks prior to enrollment.

(22) Subject has known moderate or severe persistent asthma, or currently has uncontrolled asthma of any classification.

Overview of Key Efficacy Assessments

Myeloma paraprotein

Serum immunoglobulins

Serum free light chains

Immunofixation

Corrected serum calcium

Bone marrow aspirate (BMA)/bone marrow biopsy (BMB)

Radiographic imaging assessments of lytic bone lesions

Extramedullary plasmacytomas (EMI's) assessments

Eastern Cooperative Oncology Group (ECOG) Performance Status

Overview of Key Safety Assessments

Overview of Key Safety Assessments

Adverse events (AEs) including AEs of special interest (AESIs) which would include second primary malignancies Complete physical examination including vital signs and venous thromboembolism (VTE) monitoring Clinical laboratory evaluations (hematology, serum chemistry, urinalysis)

Renal function assessments

Pancreatic function assessments (part of chemistry panel)

Ophthalmologic assessment if clinically indicated 12-lead electrocardiograms

Pregnancy testing/counseling

Concomitant medications and procedures

Overview of Pharmacokinetic Assessments

Subjects will be required to participate in sparse PK sampling as a participant in the main study. An additional subset of subjects will be assigned to participate in the intensive PK sample collection. Both intensive and sparse PK samples will be collected to evaluate Compound A-S, and as appropriate, its R-enantiomer Compound A-R in plasma.

Sparse PK sampling: Pharmacokinetic blood samples will be collected in subjects at the following time points:

Cycles 1-4, Days 8, 15: one predose sample per visit.

Intensive PK sampling: In addition to the sparse PK sampling, frequent collection of PK blood samples will be performed in approximately 1 subject per dose level. Samples will be collected at the following time points:

Cycle 1, Day 8: 2, between 4-8, and 24 hours (±5 hours) after administration of Compound A-S.

At each timepoint, approximately 3 mL of blood will be collected.

Statistical Methods

The primary objective of Part 1 of the study is to determine the MTDs/RP2Ds of Compound A in combination with dexamethasone and daratumumab in subjects with RRMM. Safety endpoints such as dose-limiting toxicity (DLT), treatment-emergent adverse events (AEs), serious AEs (SAES), and AEs of special interest (AESIs) will be summarized by dose level.

Example 2: Effect of Compound A-S, Daratumumab and the Combination of Compound A-S and Daratumumab on MM Cell Line H929

Viable peripheral blood mononuclear cells (PBMCs) from healthy donors were prepared from buffy coats (leukocytes) obtained from the NY Blood Center. Briefly, healthy donor samples were diluted 1:1 with 1×PBS+2% FBS, layered over 15 mL of Ficoll in a 50 mL conical tube and centrifuged at 450 g, at RT for 35 min. The enriched cell layer was decanted, washed with PBS and incubated with RBC lysis buffer for 5 minutes. PMBC samples were then centrifuged at 1200 RPM for 5 minutes and resuspended at $30\times10^6$ cells/mL in RPMI with 10% FBS. OKT-3 coated tissue culture plates were prepared by adding 20 ml/plate 1×PBS with 3 μg/ml OKT-3 to tissue culture plates, incubated at 37° C. for 4 hours and washed twice with 1×PBS.

H929 multiple myeloma cells were prepared by seeding at $5\times10^5$ cells/ml in 6-well plate and treated with either DMSO, 0.1 μg/ml daratumumab, 0.008 μM Compound A-S or a combination of 0.1 μg/ml daratumumab and 0.008 μM Compound A-S for 72 hrs. Previously prepared viable PBMCs were seeded at $2\times10^6$ cells/ml in OKT-3 coated plates and treated with either DMSO, 0.1 μg/ml daratumumab, 0.008 μM Compound A-S or a combination of 0.1 μg/ml daratumumab and 0.008 μM Compound A-S for 72 hrs. After 72 hrs, H929 cells were stained with CFSE (200 nM) at 37° C. for 3 minutes and resuspended at in $1\times10^6$ cells/ml in RPMI media with 10% FBS. Viable PBMCs were washed in 1× in RPMI to remove drug prior to co-culturing and resuspended at $4\times10^6$ cells/ml in RPMI with 10% FBS. Cell cultures were then combined at a PMBC to H929 ratio of 4:1 for 4 hrs. Cells were then centrifuged, washed with 1×PBS and stained with AnnxinV and To-Pro3 at RT for 10 minutes. Apoptosis was subsequently analyzed by flow cytometry gated on CFSE positive cells. FIG. 1A, depicts the effect of DMSO, 0.1 μg/ml daratumumab, 0.008 μM Compound A-S or a combination of 0.1 μg/ml daratumumab and 0.008 μM Compound A-S on cell viability.

Figure 1B:
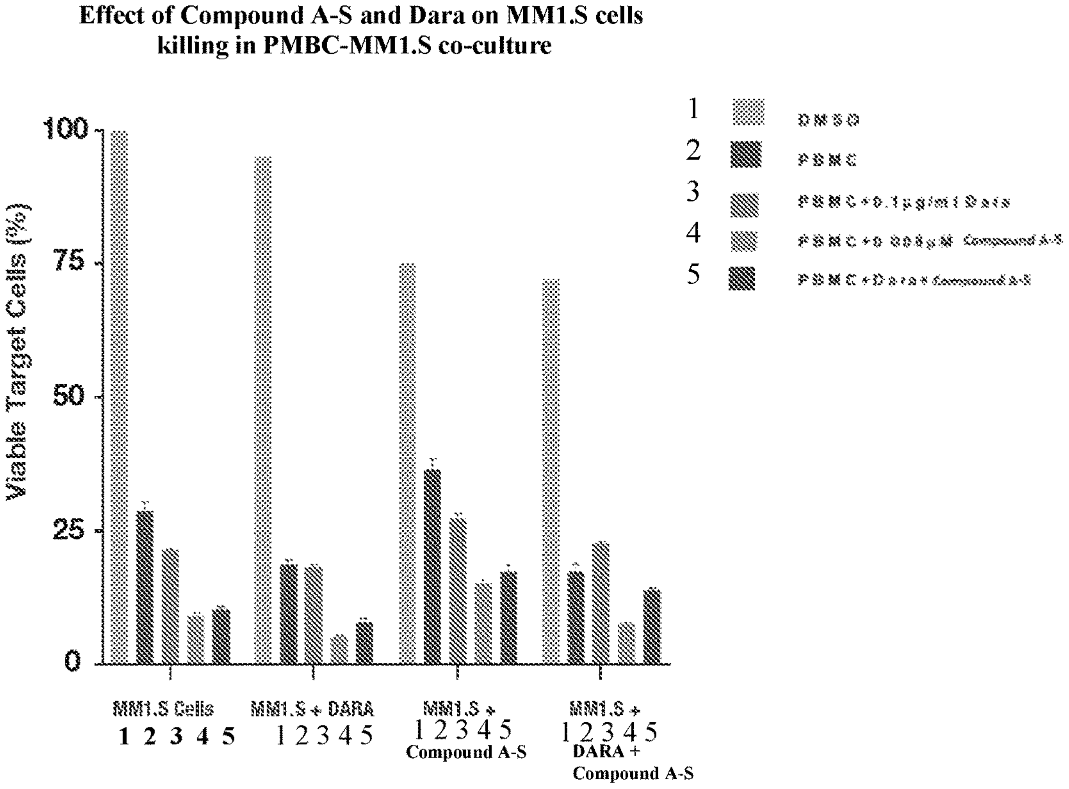
FIG. 1B depicts effects of compound A-S, daratumumab and the combination of compound A-S with daratumumab on MM cell line MM1.S.

MM1.S cells were cultured under standard conditions (Bjorklund C, et al., *Blood Cancer J.* 2015; 5:e354) and treated with either DMSO, 0.1 μg/ml daratumumab, 0.008 μM Compound A-S or a combination of 0.1 μg/ml daratumumab and 0.008 μM Compound A-S for 72 hrs. Apoptosis was subsequently analyzed by flow cytometry gated on CFSE positive cells. FIG. 1B, depicts the effect of DMSO, 0.1 μg/ml daratumumab, 0.008 μM Compound A-S or a combination of 0.1 μg/ml daratumumab and 0.008 μM Compound A-S on cell viability.

Figure 2:
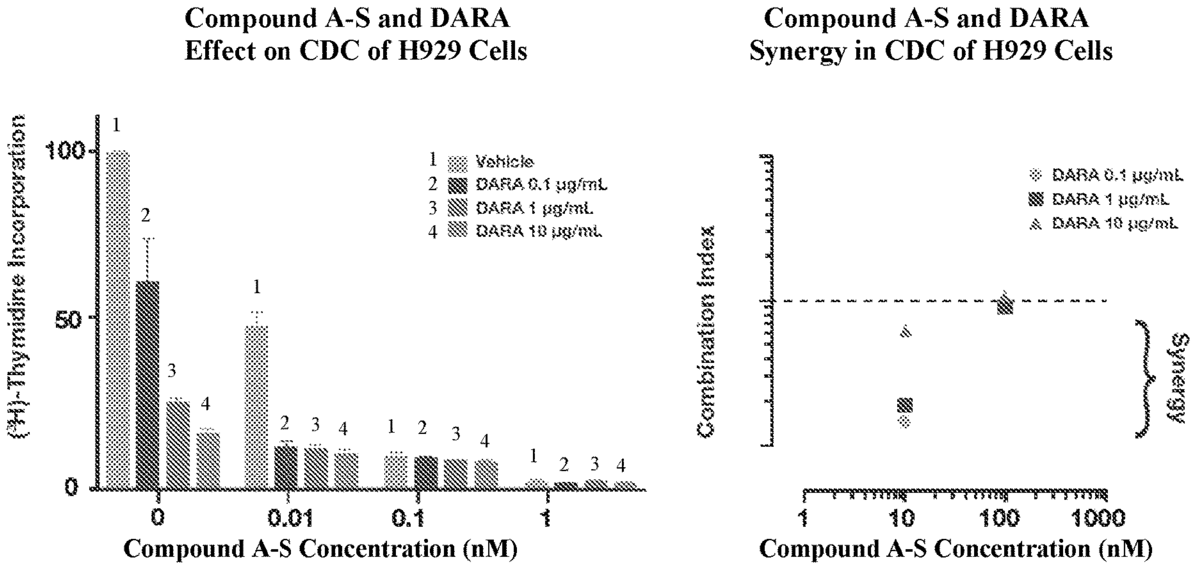
FIG. 2 depicts effects of the combination of compound A-S with daratumumab in complement-dependent cytotoxicity (CDC) assay on MM cell line H929.

Synergistic anti-myeloma cell activity was observed in complement-dependent cytotoxicity (CDC) assays, following treatment of H929 and U266 multiple myeloma cells with Compound A-S and daratumumab combination. FIG. 2, depicts the results of CDC assay, showing synergistic antiproliferative activity of Compound A-S with daratumumab in H929 cells, by the Chou-Talalay method, in which combination index (CI) of less than 1 indicates synergy.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or managing newly diagnosed multiple myeloma, comprising administering to a patient having the newly diagnosed multiple myeloma (i) Compound A Compound A

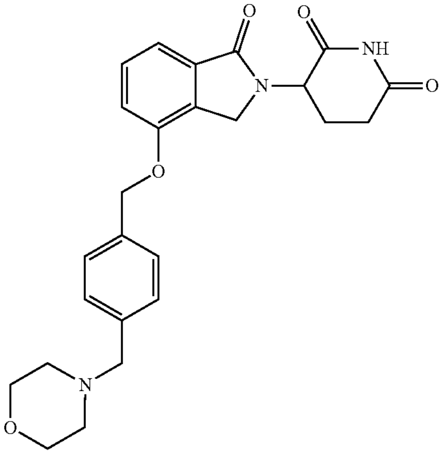 [SMILES: O=C1CC[C@H](N2Cc3c(OCc4ccc(CN5CCOCC5)cc4)cccc3C2=O)C(=O)N1]

or an enantiomer or mixture or enantiomers thereof, or a pharmaceutically acceptable salt, solvate, hydrate, co-crystal, clathrate, or polymorph thereof in an amount of from about 0.5 to about 5 mg per day and (ii) daratumumab.

2. A method of treating or managing newly diagnosed multiple myeloma, comprising administering to a patient having the newly diagnosed multiple myeloma a (i) Compound A Compound A

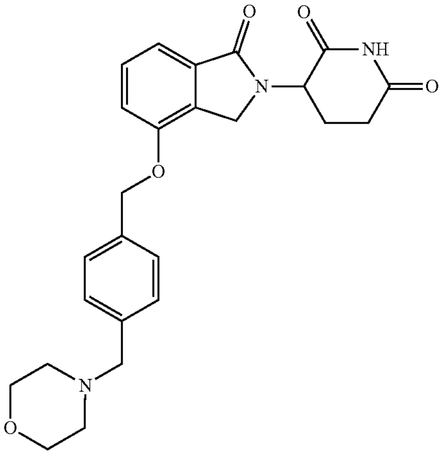

or an enantiomer or mixture of enantiomers thereof, or a pharmaceutically acceptable salt, solvate, hydrate, co-crystal, clathrate, or polymorph thereof in an amount of from about 0.5 to about 5 mg per day, (ii) daratumumab and (iii) dexamethasone, or an enantiomer or a mixture of enantiomers thereof, or a pharmaceutically acceptable salt, solvate, hydrate, co-crystal, clathrate, or polymorph thereof.

3. The method of claim 2, wherein the newly diagnosed multiple myeloma is smoldering myeloma, indolent myeloma, active multiple myeloma, extramedullary plasmacytoma, solitary plasmacytoma of the bone, light chain myeloma, or non-secretory myeloma.

4. A method for treating or managing newly diagnosed multiple myeloma, comprising:

(i) identifying a patient having the newly diagnosed multiple myeloma sensitive to treatment with (a) Compound A, or an enantiomer or mixture of enantiomers thereof, or a pharmaceutically acceptable salt, solvate, hydrate, co-crystal, clathrate, or polymorph thereof and (b) daratumumab; and (ii) administering to the patient (a) Compound A, or an enantiomer or mixture of enantiomers thereof, or a pharmaceutically acceptable salt, solvate, hydrate, co-crystal, clathrate, or polymorph thereof in an amount of from about 0.5 to about 5 mg per day and (b) daratumumab.

5. A method for treating or managing newly diagnosed multiple myeloma, comprising:

(i) identifying a patient having the newly diagnosed multiple myeloma sensitive to treatment with (a) Compound A, or an enantiomer or mixture of enantiomers thereof, or a pharmaceutically acceptable salt, solvate, hydrate, co-crystal, clathrate, or polymorph thereof (b) daratumumab and (c) dexamethasone, or an enantiomer or a mixture of enantiomers thereof, or a pharmaceutically acceptable salt, solvate, hydrate, co-crystal, clathrate, or polymorph thereof; and (ii) administering to the patient (a) Compound A, or an enantiomer or mixture of enantiomers thereof, or a pharmaceutically acceptable salt, solvate, hydrate, co-crystal, clathrate, or polymorph thereof in an amount of from about 0.5 to about 5 mg per day (b) daratumumab and (c) dexamethasone, or an enantiomer or a mixture of enantiomers thereof, or a pharmaceutically acceptable salt, solvate, hydrate, co-crystal, clathrate, or polymorph thereof.

6. The method of claim 1, wherein daratumumab is administered in an amount of from about 16 to about 200 mg/kg per day.

7. The method of claim 2, wherein (i) daratumumab is administered in an amount of from about 16 to about 200 mg/kg per day and (ii) dexamethasone, or an enantiomer or a mixture of enantiomers thereof, or a pharmaceutically acceptable salt, solvate, hydrate, co-crystal, clathrate, or polymorph thereof, is administered in an amount of from about 20 to about 200 mg.

8. The method of claim 6, wherein daratumumab is administered in an amount of from about 16 to about 25 mg/kg per day.

9. The method of claim 6, wherein (i) Compound A, or an enantiomer or mixture of enantiomers thereof, or a pharmaceutically acceptable salt, solvate, hydrate, co-crystal, clathrate, or polymorph thereof, is administered in an amount of about 0.75, 1, 1.3, or 1.6 mg per day, and (ii) daratumumab is administered in an amount of about 16, 20, 25, 30, 35, 40, 45, 50, 75, 100, 150 or 200 mg/kg per day.

10. The method of claim 6, wherein (i) Compound A, or an enantiomer or mixture of enantiomers thereof, or a pharmaceutically acceptable salt, solvate, hydrate, co-crystal, clathrate, or polymorph thereof is administered orally and (ii) daratumumab is administered intravenously.

11. The method of claim 6, wherein (i) Compound A, or an enantiomer or mixture of enantiomers thereof, or a pharmaceutically acceptable salt, solvate, hydrate, co-crystal, clathrate, or polymorph thereof is administered in a capsule or tablet and (ii) daratumumab is administered by injection or infusion.

12. The method of claim 11, wherein (i) Compound A, or an enantiomer or mixture of enantiomers thereof, or a pharmaceutically acceptable salt, solvate, hydrate, co-crystal, clathrate, or polymorph thereof is administered in a capsule and (ii) daratumumab is administered as intravenous infusion of diluted 20 mg/ml single dose vial.

13. The method of claim 7, wherein (i) daratumumab is administered in an amount of from about 16 to about 25 mg/kg per day and (ii) dexamethasone is administered in an amount of from about 20 to about 50 mg per day.

14. The method of claim 7, wherein (i) Compound A, or an enantiomer or mixture of enantiomers thereof, or a pharmaceutically acceptable salt, solvate, hydrate, co-crystal, clathrate, or polymorph thereof, is administered in an amount of about 0.75, 1, 1.3, or 1.6 mg per day, (ii) daratumumab is administered in an amount of about 16, 20, 25, 30, 35, 40, 45, 50, 75, 100, 150 or 200 mg/kg per day and (iii) dexamethasone, or an enantiomer or a mixture of enantiomers thereof, or a pharmaceutically acceptable salt, solvate, hydrate, co-crystal, clathrate, or polymorph thereof, is administered in an amount of about 20, 25, 30, 35, 40, 45, 50, 75, 100, 150 or 200 mg per day.

15. The method of claim 7, wherein (i) Compound A, or an enantiomer or mixture of enantiomers thereof, or a pharmaceutically acceptable salt, solvate, hydrate, co-crystal, clathrate, or polymorph thereof is administered orally, (ii) daratumumab is administered intravenously and (iii) dexamethasone is administered orally or by injection.

16. The method of claim 7, wherein (i) Compound A, or an enantiomer or mixture of enantiomers thereof, or a pharmaceutically acceptable salt, solvate, hydrate, co-crystal, clathrate, or polymorph thereof is administered in a capsule or tablet, (ii) daratumumab is administered by injection or infusion and (iii) dexamethasone is administered in a tablet.

17. The method of claim 16, wherein (i) Compound A, or an enantiomer or mixture of enantiomers thereof, or a pharmaceutically acceptable salt, solvate, hydrate, co-crystal, clathrate, or polymorph thereof is administered in a capsule, (ii) daratumumab is administered as intravenous infusion of diluted 20 mg/ml single dose vial and (iii) dexamethasone is administered as 0.5 mg or 0.75 mg of a tablet.

18. The method of claim 1, wherein the compounds are administered in a 28 day cycle.

19. The method of claim 1, wherein the compound is Compound A-S

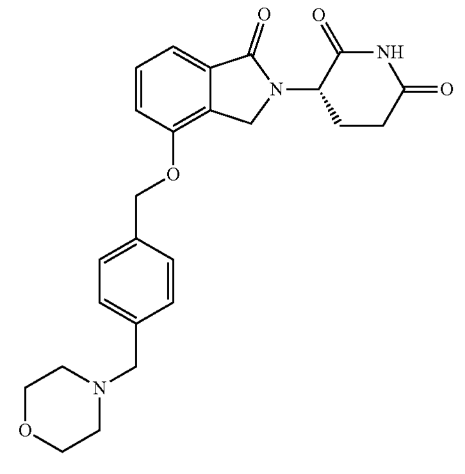

or a pharmaceutically acceptable salt, solvate, hydrate, co-crystal, clathrate, or polymorph thereof.

* * * * *